(12) United States Patent
Shmayahu et al.

(10) Patent No.: US 11,464,422 B2
(45) Date of Patent: Oct. 11, 2022

(54) CORONARY SINUS-BASED ELECTROMAGNETIC MAPPING

(71) Applicant: Navix International Limited, Road Town (VG)

(72) Inventors: Yizhaq Shmayahu, Ramat-HaSharon (IL); Yitzhack Schwartz, Haifa (IL); Eli Dichterman, Haifa (IL); Zalman Ibragimov, Rehovot (IL); Shlomo Ben-Haim, Milan (IT); Yehonatan Ben David, Tel-Aviv (IL)

(73) Assignee: Navix Internatonal Limited, Road Town (VG)

( * ) Notice: Subject to any disclaimer, the term of this patent is extended or adjusted under 35 U.S.C. 154(b) by 558 days.

(21) Appl. No.: 16/478,486

(22) PCT Filed: Jan. 17, 2018

(86) PCT No.: PCT/IB2018/050289
§ 371 (c)(1),
(2) Date: Jul. 17, 2019

(87) PCT Pub. No.: WO2018/134747
PCT Pub. Date: Jul. 26, 2018

(65) Prior Publication Data
US 2019/0365280 A1    Dec. 5, 2019

Related U.S. Application Data

(60) Provisional application No. 62/449,055, filed on Jan. 22, 2017.

(51) Int. Cl.
*A61B 5/06* (2006.01)
*A61B 34/10* (2016.01)
(Continued)

(52) U.S. Cl.
CPC .............. *A61B 5/068* (2013.01); *A61B 5/063* (2013.01); *A61B 5/7253* (2013.01);
(Continued)

(58) Field of Classification Search
CPC ...... A61B 18/1492; A61B 2018/00267; A61B 2018/00357; A61B 2018/00577;
(Continued)

(56) References Cited

U.S. PATENT DOCUMENTS 6,266,552 B1    7/2001  Slettenmark
2011/0282186 A1   11/2011  Harley et al.
(Continued)

FOREIGN PATENT DOCUMENTS

WO    WO 2018/134747    7/2018

OTHER PUBLICATIONS

International Preliminary Report on Patentability dated Aug. 1, 2019 From the International Bureau of WIPO Re. Application No. PCT/IB2018/050289. (9 Pages).
(Continued)

*Primary Examiner* — Mark D Remaly

(57) ABSTRACT

In some embodiments, a body cavity shape of a subject is reconstructed based on intrabody measurements of at least one property of an electromagnetic field by an intrabody probe (for example, a catheter probe) moving within a plurality of electrical fields intersecting the body cavity. In some embodiments, the electrical fields are generated at least in part from electrodes positioned in close proximity, for example, within 1 cm, of the body cavity. In some embodiments, the body cavity is a chamber of a heart (for example, a left atrium or left ventricle), and the electrodes used to generate the electrical field are positioned in the coronary sinus, a large vein occupying the groove between the left atrium and left ventricle. In some embodiments,
(Continued)

known distances between measuring electrodes are used in guiding reconstruction, potentially overcoming difficulties of reconstruction from measurements of non-linear electrical fields.

26 Claims, 9 Drawing Sheets

(51) Int. Cl.
  *A61B 5/00*   (2006.01)
  *A61B 18/14*   (2006.01)
  *A61B 18/00*   (2006.01)

(52) U.S. Cl.
  CPC .......... *A61B 18/1492* (2013.01); *A61B 34/10* (2016.02); *A61B 2018/00267* (2013.01); *A61B 2018/00357* (2013.01); *A61B 2018/00577* (2013.01); *A61B 2018/00875* (2013.01); *A61B 2018/00892* (2013.01); *A61B 2034/105* (2016.02); *A61B 2034/107* (2016.02)

(58) Field of Classification Search
  CPC ........... A61B 2018/00875; A61B 2018/00892; A61B 2034/105; A61B 2034/107; A61B 34/10; A61B 5/063; A61B 5/065; A61B 5/068; A61B 5/287; A61B 5/6852; A61B 5/7253
  See application file for complete search history.

(56) References Cited

U.S. PATENT DOCUMENTS

2014/0024911 A1  1/2014  Harley et al.
2015/0223757 A1  8/2015  Werneth et al.

OTHER PUBLICATIONS

International Search Report and the Written Opinion dated Jun. 7, 2018 From the International Searching Authority Re. Application No. PCT/IB2018/050289. (16 Pages).

CORONARY SINUS-BASED ELECTROMAGNETIC MAPPING

RELATED APPLICATIONS

This application is a National Phase of PCT Patent Application No. PCT/IB2018/050289 having International filing date of Jan. 17, 2018, which claims the benefit of priority under 35 USC § 119(e) of U.S. Provisional Application No. 62/449,055 filed on Jan. 22, 2017. The contents of the above applications are all incorporated by reference as if fully set forth herein in their entirety.

FIELD AND BACKGROUND OF THE INVENTION

The present invention, in some embodiments thereof, relates to the field of navigation of body cavities by intra-body probes, and/or to reconstruction of body cavity shape from measurements by intra-body probes.

Several medical procedures in cardiology and other medical fields comprise the use of intrabody probes such as catheter probes to reach tissue targeted for diagnosis and/or treatment while minimizing procedure invasiveness. Early imaging-based techniques (such as fluoroscopy) for navigation of the catheter and monitoring of treatments continue to be refined, and are now joined by techniques such as electromagnetic field-guided position sensing systems.

The coronary sinus (CS) is relatively large diameter vein which collects blood from the heart muscle (myocardium) and delivers it to the right atrium. The CS extends along the outer wall of the myocardium in an arc extending from the right atrium approximately along the boundary between the left atrium and the left ventricle.

SUMMARY OF THE INVENTION

There is provided, in accordance with some embodiments of the present disclosure, a method of estimating a position of a first probe within a body cavity, the first probe comprising a plurality of sensors, the method comprising: measuring, using the plurality of sensors of the first probe, at least one property of each of a plurality of crossing electromagnetic fields generated by electrodes of a second probe positioned adjacent to the body cavity; and estimating a position of the first probe in the body cavity, based on the measuring.

In some embodiments, the estimating comprises: assigning positions to the measured at least one property to create a reconstruction of a shape of the body cavity; and estimating the position of the first probe relative to the reconstruction, based on the measuring of the at least one property at the position.

In some embodiments, the at least one measured property comprises one or more of voltages and impedances of the crossing electromagnetic fields.

In some embodiments, the estimating comprises using a cost function to find a transform that transforms measurements of the at least one property to positions, wherein the cost function assigns a greater penalty to sudden changes in the transform than to gradual changes in the transform.

In some embodiments, at least two of the plurality of sensors are spaced at a known distance from each other on the first probe, and wherein the assigning assigns a cost to distances in the reconstruction according to their difference from the known distance.

In some embodiments, the second probe is positioned in a coronary sinus, and wherein the body cavity comprises a heart chamber adjacent to the coronary sinus.

In some embodiments, the heart chamber comprises a left atrium.

In some embodiments, the heart chamber comprises a left ventricle.

In some embodiments, the assigning comprises registration of the shape of the body cavity is to a 3-D model of the body cavity.

In some embodiments, the 3-D model of the body cavity is based on data comprising one or more images of the body cavity.

In some embodiments, the 3-D model of the body cavity is based on atlas information.

In some embodiments, the plurality of crossing electromagnetic fields comprise at least three crossing electrical fields.

In some embodiments, the plurality of crossing electromagnetic fields comprise at least 10 distinguishable electrical fields.

In some embodiments, each of the plurality of crossing electromagnetic fields oscillates at a different frequency.

In some embodiments, at least one of the plurality of crossing electromagnetic fields is generated using a first plurality of electrodes of the second probe, the first plurality operating at a same frequency and a same phase.

In some embodiments, the electromagnetic field generated using the first plurality of electrodes of the second probe is generated also using a second plurality of electrodes of the second probe; wherein the second plurality of electrodes of the second probe operate at the same frequency as the first plurality of electrodes and at a phase different than the phase of the first plurality of electrodes.

In some embodiments, a body surface electrode of the second probe acts as a ground electrode relative to at least one of the electrodes of the second probe.

In some embodiments, the first probe comprises an ablation probe for ablation of tissue.

In some embodiments, at least one of the electrodes of the second probe generating at least one of the plurality of crossing electromagnetic fields is positioned within 2 cm of the position of the first probe while it is within the body cavity.

In some embodiments, at least four electrodes of the second probe generate at least one of the plurality of crossing electromagnetic fields positioned within 2 cm of the body cavity.

In some embodiments, all voltage isopotential surfaces from electromagnetic fields (a) within at least a 1 cubic centimeter portion of the body cavity and (b) used for the estimating a position curve inside the portion of the body cavity with a radius of 10 cm or less.

In some embodiments, at least one of the first probe and the second probe comprises a probe of a catheter.

There is provided, in accordance with some embodiments of the present disclosure, a system comprising: a first catheter; a second catheter; an electromagnetic field generator configured to generate a plurality of crossing electromagnetic fields through intrabody electrodes of the second catheter; and computer circuitry, configured to: receive measurements of at least one property of the crossing electromagnetic fields measured by electrodes of the first catheter; and estimate a position of the first catheter in the body cavity, based on the measurements.

There is provided, in accordance with some embodiments of the present disclosure, a system for the estimation of positions of a first probe in an intrabody position using measurements of a plurality of crossing electromagnetic fields generated by intrabody electrodes of a second probe in an intrabody position, the system comprising: computer circuitry, configured to: receive measurements of at least one property of the crossing electromagnetic fields measured by electrodes of the first probe; and estimate a position of the first probe in the body cavity, based on the measurements.

There is provided, in accordance with some embodiments of the present disclosure, a method of correcting placement of an intrabody electrode array, the method comprising: positioning the intrabody electrode array in a target position; measuring baseline voltages, using a plurality of electrodes of the intrabody electrode array to measure voltages generated by the plurality of electrodes; re-measuring voltages generated by the plurality of electrodes using the plurality of electrodes; detecting a difference between the re-measured voltage measurements and the baseline voltage measurements; repositioning the electrode array; and repeating the re-measuring and the detecting to reduce differences between new re-measured voltage measurements, and the baseline voltage measurements.

In some embodiments, the intrabody electrode array comprises a plurality of electrodes along a portion of a catheter.

In some embodiments, the plurality of electrodes are spaced along a longitudinal axis of the catheter.

In some embodiments, the target position of the electrode array comprises a coronary sinus.

There is provided, in accordance with some embodiments of the present disclosure, a method of correcting placement of an intrabody electrode array, comprising: positioning a first electrode in an intrabody position; positioning the electrode array in a target position; measuring baseline voltages between a plurality of electrodes in the electrode array and the first electrode; re-measuring voltages between the plurality of electrodes and the first electrode; detecting a difference between the re-measured voltages and the baseline voltages; and repositioning the electrode array and repeating the re-measuring and the detecting to reduce differences between new re-measured voltage measurements, and the baseline voltage measurements.

In some embodiments, the voltage measured is from an electrical field generated by the intrabody electrode array.

In some embodiments, the intrabody electrode array comprises a plurality of electrodes assembled to a catheter.

In some embodiments, the target position of the electrode array comprises a coronary sinus.

There is provided, in accordance with some embodiments of the present disclosure, a method of estimating a position of a first probe within a body cavity, the first probe comprising a plurality of sensors, the method comprising: measuring electrical characteristics using the sensors of the first probe, the measuring comprising sensing of a plurality of crossing electrical fields generated from electrodes of a second probe positioned adjacent to the body cavity; and estimating a position of the first probe in the body cavity, based on the measuring.

In some embodiments, each of the plurality of crossing electrical fields oscillates at a different frequency.

In some embodiments, the second probe is positioned in a coronary sinus, and wherein the body cavity comprises a heart chamber adjacent to the coronary sinus.

In some embodiments, the heart chamber comprises a left atrium.

In some embodiments, the heart chamber comprises a left ventricle.

In some embodiments, at least one of the plurality of crossing electrical fields is generated using a first plurality of electrodes of the second probe operating at a same frequency and a same phase.

In some embodiments, the electrical field generated using the first plurality of electrodes is generated also using a second plurality of electrodes of the second probe operating at the same frequency as the first plurality of electrodes, and at a different phase than the phase of the first plurality of electrodes.

In some embodiments, a body surface electrode acts as a ground electrode relative to at least one of the electrodes of the second probe.

In some embodiments, the first probe comprises an ablation probe for ablation of tissue.

There is provided, in accordance with some embodiments of the present disclosure, a method of reconstructing a shape of a body cavity by a first probe positioned in the body cavity, the first probe comprising a plurality of sensors, the method comprising: measuring electrical characteristics using the sensors of the first probe, the measuring comprising sensing of a plurality of crossing electrical fields generated from electrodes of a second probe positioned adjacent to the body cavity; and reconstructing the body cavity, based on the measuring.

In some embodiments, each of the plurality of crossing electrical fields oscillates at a different frequency.

In some embodiments, the electrical characteristics comprise voltages.

In some embodiments, the reconstruction of the shape of the body cavity is registered to a 3-D model of the body cavity.

In some embodiments, the 3-D model of the body cavity is based on imaging data imaging the body cavity.

In some embodiments, the 3-D model of the body cavity is based on atlas information.

There is provided, in accordance with some embodiments of the present disclosure, a method of estimating a position of a first probe within a body cavity, the first probe comprising a plurality of sensors, the method comprising: receiving measurements of crossing electrical fields using the sensors of the first probe, wherein the plurality of crossing electrical fields are generated from electrodes of a second probe positioned adjacent to the body cavity; and estimating a position of the first probe in the body cavity, based on the measurements.

There is provided, in accordance with some embodiments of the present disclosure, a method of reconstructing a body cavity, the method comprising: receiving measurements of crossing electrical fields using sensors of a first probe within the body cavity, wherein the plurality of crossing electrical fields are generated from electrodes of a second probe positioned adjacent to the body cavity; and reconstructing the body cavity, based on the measurements.

There is provided, in accordance with some embodiments of the present disclosure, a method of estimating a position of a first probe within a body cavity, the first probe comprising a plurality of sensors, the method comprising: receiving electrical characteristics measurements using the sensors of the first probe, the measuring comprising sensing of a plurality of crossing electrical fields generated from electrodes of a second probe positioned adjacent to the body cavity; and estimating a position of the first probe in the body cavity, based on the measurements.

In some embodiments, the plurality of crossing electrical fields oscillates at a plurality of frequencies.

In some embodiments, the measurements include voltage measurements.

In some embodiments, the voltage indicates impedance.

In some embodiments, the measurements include impedance measurements.

According to some embodiments of the present disclosure, the second probe is positioned in a coronary sinus, and the body cavity comprises a heart chamber adjacent to the coronary sinus.

There is provided, in accordance with some embodiments of the present disclosure, a method of estimating a position of a first probe within a body cavity, the first probe comprising a plurality of sensors, the method comprising: measuring voltages using the sensors of the first probe, the voltages being due to a plurality of crossing electrical fields generated from electrodes of a second probe positioned adjacent to the body cavity; and estimating a position of the first probe in the body cavity, based on the measuring.

According to some embodiments of the present disclosure, the estimating comprises: assigning positions to the measured voltages to create a reconstruction of a shape of the body cavity; and estimating the position of the first probe relative to the reconstruction, based on voltages measured at the position.

According to some embodiments of the present disclosure, the assigning comprises constraining regions where close voltages are measured to coherently correspond to spatially close regions in the reconstruction.

According to some embodiments of the present disclosure, the plurality of sensors are spaced at known distances from each other on the first probe, and wherein the assigning comprises constraining distances in the reconstruction to be substantially equal to the known distances, for voltage measurements taken from different sensors of the plurality of sensors while the first probe remains substantially in one position.

According to some embodiments of the present disclosure, the second probe is positioned in a coronary sinus, and wherein the body cavity comprises a heart chamber adjacent to the coronary sinus.

According to some embodiments of the present disclosure, the heart chamber comprises a left atrium.

According to some embodiments of the present disclosure, the heart chamber comprises a left ventricle.

According to some embodiments of the present disclosure, the reconstruction of the shape of the body cavity is registered to a 3-D model of the body cavity.

According to some embodiments of the present disclosure, the 3-D model of the body cavity is based on imaging data imaging the body cavity.

According to some embodiments of the present disclosure, the 3-D model of the body cavity is based on 3-D atlas data.

According to some embodiments of the present disclosure, the plurality of crossing electrical fields comprises at least three crossing electrical fields.

According to some embodiments of the present disclosure, the plurality of crossing electrical fields comprises at least 10 crossing electrical fields.

According to some embodiments of the present disclosure, each of the plurality of crossing electrical fields oscillates at a different frequency.

According to some embodiments of the present disclosure, at least one of the plurality of crossing electrical fields is generated using a first plurality of electrodes of the second probe operating at the same phase and frequency.

According to some embodiments of the present disclosure, the electrical field generated using the first plurality of electrodes is generated also using a second plurality of electrodes of the second probe operating at the same frequency as and a phase different than the first plurality of electrodes.

According to some embodiments of the present disclosure, a body surface electrode acts as a ground electrode for at least one of the plurality of crossing electrical fields generated from electrodes of the second probe.

According to some embodiments of the present disclosure, the first probe comprises an ablation probe for ablation of tissue.

According to some embodiments of the present disclosure, at least one of the electrodes of the second probe generating at least one of the plurality of crossing electrical fields is positioned within 2 cm of the position of the first probe while it is within the body cavity.

According to some embodiments of the present disclosure, at least four electrodes of the second probe generate at least one of the plurality of crossing electrical fields positioned within 2 cm of the body cavity.

According to some embodiments of the present disclosure, all voltage isopotential surfaces from electrical fields within at least a 1 cubic centimeter portion of the body cavity used for the estimating curve with a radius of 10 cm or less.

According to some embodiments of the present disclosure, at least one of the first probe and the second probe comprises a probe of a catheter.

According to some embodiments of the present disclosure, the electrical fields generated within the body cavity from electrodes of the second probe are highly non-linear.

There is provided, in accordance with some embodiments of the present disclosure, a system comprising a first electrode catheter, a second electrode catheter, and an electrical field generator; wherein the electrical field generator is configured to generate a plurality of crossing electrical fields through intrabody electrodes of the second catheter while using voltages of the crossing electrical fields sensed by the first catheter to estimate a position of the first catheter.

There is provided, in accordance with some embodiments of the present disclosure, the system above, further comprising a processor configured to perform the estimating of any one of the methods described above.

There is provided, in accordance with some embodiments of the present disclosure, a method of maintaining registration of an intrabody electrode array, comprising: positioning the electrode array in a target position; measuring baseline voltages between a plurality of electrodes in the electrode array; re-measuring voltages between the plurality of electrodes; detecting a difference between the re-measured voltages and the baseline voltages; and repositioning the electrode array for a reduced difference between new voltage measurements between the plurality of electrodes, and the baseline voltages.

According to some embodiments of the present disclosure, the electrode array comprises a plurality of electrodes assembled to a catheter.

According to some embodiments of the present disclosure, the plurality of electrodes is spaced along a longitudinal axis of the catheter.

According to some embodiments of the present disclosure, the target position of the electrode array comprises a coronary sinus.

There is provided, in accordance with some embodiments of the present disclosure, a method of maintaining registration of an intrabody electrode array, comprising: positioning the electrode array in a target position; positioning a reference electrode in an intrabody position; measuring baseline voltages between a plurality of electrodes in the electrode array and the reference electrode; re-measuring voltages between the plurality of electrodes and the reference electrode; detecting a difference between the re-measured voltages and the baseline voltages; and repositioning the electrode array for a reduced difference between new voltage measurements between the plurality of electrodes and the reference electrode, and the baseline voltages.

According to some embodiments of the present disclosure, the voltage measured is from an electrical field generated by the electrode array.

According to some embodiments of the present disclosure, the electrode array comprises a plurality of electrodes assembled to a catheter.

According to some embodiments of the present disclosure, the target position of the electrode array comprises a coronary sinus.

There is provided, in accordance with some embodiments of the present disclosure, a method of estimating a position of a first probe within a body cavity, the first probe comprising a plurality of sensors, the method comprising: measuring electrical characteristics using the sensors of the first probe, the measuring comprising sensing of a plurality of crossing electrical fields generated from electrodes of a second probe positioned adjacent to the body cavity; and estimating a position of the first probe in the body cavity, based on the measuring.

According to some embodiments of the present disclosure, each of the plurality of crossing electrical fields oscillates at a different frequency.

According to some embodiments of the present disclosure, the second probe is positioned in a coronary sinus, and wherein the body cavity comprises a heart chamber adjacent to the coronary sinus.

According to some embodiments of the present disclosure, the heart chamber comprises a left atrium.

According to some embodiments of the present disclosure, the heart chamber comprises a left ventricle.

According to some embodiments of the present disclosure, the plurality of crossing electrical fields comprises at least 10 crossing electrical fields.

According to some embodiments of the present disclosure, at least one of the plurality of crossing electrical fields is generated using a first plurality of electrodes of the second probe operating at the same phase and frequency.

According to some embodiments of the present disclosure, the electrical field generated using the first plurality of electrodes is generated also using a second plurality of electrodes of the second probe operating at the same frequency as and a phase different than the first plurality of electrodes.

According to some embodiments of the present disclosure, a body surface electrode acts as a ground electrode for at least one of the plurality of crossing electrical fields generated from electrodes of the second probe.

According to some embodiments of the present disclosure, the first probe comprises an ablation probe for ablation of tissue.

There is provided, in accordance with some embodiments of the present disclosure, a method of reconstructing a shape of a body cavity by a first probe positioned in the body cavity, the first probe comprising a plurality of sensors, the method comprising: measuring electrical characteristics using the sensors of the first probe, the measuring compris-ing sensing of a plurality of crossing electrical fields generated from electrodes of a second probe positioned adjacent to the body cavity; and reconstructing the body cavity, based on the measuring.

According to some embodiments of the present disclosure, each of the plurality of crossing electrical fields oscillates at a different frequency.

According to some embodiments of the present disclosure, the electrical characteristics comprise voltages.

According to some embodiments of the present disclosure, the reconstruction of the shape of the body cavity is registered to a 3-D model of the body cavity.

According to some embodiments of the present disclosure, the 3-D model of the body cavity is based on imaging data imaging the body cavity.

According to some embodiments of the present disclosure, the 3-D model of the body cavity is based on 3-D atlas data.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system" (e.g., a method may be implemented using "computer circuitry"). Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well. Any of these implementations are referred to herein more generally as instances of computer circuitry.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example, and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
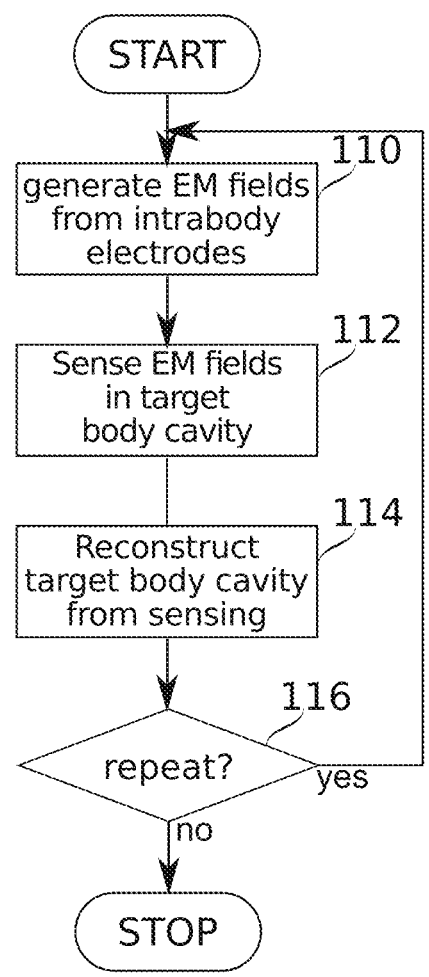
FIG. 1 is a schematic flowchart of a method for reconstruction and/or navigation within a target body cavity, according to some embodiments of the present disclosure.

The present invention, in some embodiments thereof, relates to the field of navigation of body cavities by intra-body probes, and/or to reconstruction of body cavity shape from measurements by intra-body probes.

As used herein, the term "reconstruction" is used (as are related word forms, e.g., "reconstruct" and "reconstructing") to indicate a process of and/or process product from the generation of a representation of a three dimensional (3-D) shape of a target (e.g., body cavity). In some embodiments, reconstruction comprises mapping from a set of measurements (e.g., measurements of a plurality of distinguishable electromagnetic fields) to corresponding positions in a physical space at which those measurements are made.

Overview

An aspect of some embodiments of the present disclosure relates to use of a first intrabody probe to generate reference electromagnetic fields for use in estimating the position of a second probe within a body cavity. In some embodiments, the estimate is based on measurements of the reference electromagnetic fields by the second intrabody probe. In some embodiments, the positions estimated are used, for example, in reconstruction of and/or navigation in the body cavity. Herein, estimating a set of positions within a body cavity is also referred to as a "reconstructing" the body cavity or a portion thereof, whether or not a surface is reconstructed from the estimated positions. As used herein the term "probe" and "intrabody probe" are used interchangeably.

In some embodiments, the first intrabody probe comprises a catheter bearing a plurality of electrodes, e.g., electrodes inserted into the coronary sinus (CS) of a patient's heart, or another lumen of the heart and/or in proximity to the heart (for example, an esophagus or coronary blood vessel). Herein, electrodes joined together on a single device such as a catheter probe are optionally referred to as an "electrode array". A second intrabody probe (e.g., an ablation catheter)—e.g., within a lumen of the heart such as the left atrium (LA))—senses voltages (or another measured property) within time-varying fields generated at a plurality of distinct frequencies (e.g., between about 10 kHz and about 1 MHz) by electrodes of the first probe. In some embodiments, the body cavity comprises another lumen of the heart (e.g., left ventricle). In some embodiments, the body cavity, within which positions of a catheter are estimated, is a cavity of another organ such as the brain (e.g. brain ventricle), digestive system (lumens of the stomach and/or intestines), lung, etc. In some embodiments, electrodes used for generating electromagnetic fields are placed in any of these intrabody locations, and/or another position such as the esophagus, nasal cavity, etc. Herein "positions" refer to positions in a physical space (including in representations of physical space such as models and/or reconstructions of a real-world physical space). Optionally, positions refer to three-dimensional positions in a physical space. Optionally, positions may be defined in a different coordinate system. For example, positions along a surface extending through a three-dimensional physical space may be defined parametrically in two dimensions relative to a coordinate system defined by the surface.

Optionally, an electromagnetic field is measured directly or indirectly with respect to any electrical characteristic of the electromagnetic field itself (such as voltage, phase and/or amplitude), and/or of the environment of the electromagnetic field; for example, an electrical characteristic such as impedance or dielectric properties of material in the electromagnetic field. Herein, electromagnetic fields may be referred to more particularly as electrical fields, e.g., in reference to properties which are specifically electrical in nature. Voltage measurements are used herein as examples, however it should be understood that any suitable measurement of an electromagnetic field (and optionally a suitable magnetic measurement, rather than an electric measurement) may be used. In some embodiments, measuring at least one property of a plurality of crossing electromagnetic fields may comprise or refer to measuring of the electromagnetic fields, e.g., voltage and/or impedance measurements. In some embodiments, voltage measurements (optionally combined with current estimates) are expressed as impedance, dielectric, and/or resistance values. Currents may be estimated, in some embodiments, based on operational setups of the field generator. In some embodiments, voltage measurements and/or impedance measurements may serve as measurements of electromagnetic fields, and as such should also be understood to also comprise measurement of electromagnetic fields (optionally, measurements of time-varying voltage are used as indications of impedance). More generally, any parameter characterizing an electromagnetic field (that is, parameters which are electrical or magnetic in nature) may serve to measure the electromagnetic fields. In some embodiments, measuring electrical characteristics may comprise or refer to measuring of the electromagnetic fields, e.g., voltage and/or impedance measurements. In some embodiments, measuring at least one property of a plurality of crossing electromagnetic fields may comprise or refer to measuring of the electromagnetic fields, e.g., voltage and/or impedance measurements.

As the second probe moves, the sensed voltages change as well. For example, impedance associated with a single electrode (determined based on the current estimated to run in the electrode and the voltage the electrode measures at the frequency it transmits) may vary from one position to another by a factor of between about 2 to about 1000. In some cases (e.g., inside the blood pool of a heart chamber), the impedance may stay substantially the same at different positions. The sensed voltages can be used to navigate the second probe, and/or to create a reconstruction of the shape of the lumen within which the second probe is moving. Herein, an electrode is said to "generate" an electromagnetic field when it serves as current source or sink for the electromagnetic field. An electrode or set of electrodes said to "generate" an electromagnetic field are not limited thereby to be the only electrodes involved in generation of the electromagnetic field. An electrode is said to "measure" or "sense" an electromagnetic field by measuring a voltage which can be read out by a recording device. The voltage may be a result of electrical current passing through the electrode upon exposure to the electromagnetic field.

Intrabody positions, at which electromagnetic field generating electrodes used in navigation of heart chambers are placed, optionally comprise, for example, the CS, esophagus, septal walls, and/or heart chambers adjacent to a heart chamber to be navigated. Adjacent to may be understood, for example, to mean within 5 cm, 3 cm, 2 cm, 1 cm. Additionally or alternatively, adjacent (in the case of adjacent lumens such as heart cavities and/or blood vessels) may be understood to mean separated from one another by a wall of tissue, optionally without an intervening lumen. These definitions of adjacency also apply to the term "proximity" as the term is used herein. The CS, located near the relatively immobile boundary between the left atrium and the left ventricle (atrioventricular groove), marks a relatively stable position in the heart (particularly with respect to the left atrium and left ventricle). Compared to the use of body surface electrodes, it is a potential advantage to place electromagnetic field generating electrodes in intrabody positions due to potentially greater electrical stability (e.g., lessened effects from movements of the body and/or changes in contact resistance), and/or closer proximity (e.g., steeper voltage gradients may be obtained for the same current level, and/or there may be lowered influence on electromagnetic fields from body parts remote from the sensing positions). In some embodiments, the electrodes which generate fields are placed along an intrabody curve. In some embodiments, the intrabody curve along which the field-generating electrodes are placed extends (within a first lumen) around at least 25%, 33%, 50%, or another fraction of a circumference of another lumen in which measurements for the determination of position are to be made. In some embodiments, the lumen in which the field-generating electrodes are placed confines the electrodes so that they are restricted to remain in one position, and/or within a range of positions that can be selected among by simply advancing or retracting the electrodes along a path (e.g., by advancing or retracting a catheter on which the electrodes are mounted).

Some Issues Affecting use of Fields Generated from the CS in Reconstruction and/or Navigation Though their use as voltage-sensing references is recognized, electrodes in the CS are potentially problematic with respect to their production of electromagnetic fields useful in reconstruction and/or navigation. In particular, CS-originated electromagnetic fields are potentially highly non-linear in the adjoining LA and other heart chambers (e.g., at positions within 10-20 mm from electromagnetic field generating electrodes), compared, e.g., to fields generated from distances further away (e.g., 5 cm or more), and/or generated from spatially extended electrodes such as body surface electrodes (5-10 cm, for example, as opposed to limits of 1-5 mm for intrabody body electrodes). Voltage isopotential surfaces of the electromagnetic fields, rather than being roughly planar in the region of interest, tend to be highly curved, so that an electrode moving straight in positional space encounters a curved, and potentially even reversing path in voltage space. In some embodiments, a radius of curvature of voltage isopotential surfaces within the target body cavity (and used for reconstruction of a shape of the target body cavity) is less about 1 cm, 2 cm, 3 cm, 4 cm, 5 cm, or another radius. In some embodiments, there are reconstructed regions of the target body cavity in which no voltage isopotential surface has a radius larger than about 3 cm, 4 cm, 5 cm, 8 cm, 10 cm, or another smaller or intermediate radius. In some embodiments, voltage isopotential surfaces from only one or two electromagnetic fields have a radius larger than one of the aforesaid radii, while the voltage isopotential surfaces of every second, third, and following electromagnetic field (if defined) is confined to a smaller radius value. In some embodiments, the reconstructed regions indicated in the preceding two sentences comprise at least 1 cubic centimeter ($cm^3$), 4 $cm^3$, 8 $cm^3$, or another larger or intermediate volume.

Even moving exactly in the gradient direction (perpendicular to voltage isopotential surfaces), an electrode may encounter voltage changes as a function of position which are exponential, rather than linear.

Non-linearity creates a number of problems for using such fields to establish a voltage-based coordinate system. First, the fields are not naturally close to defining a Cartesian-type coordinate system wherein each uniform step in voltage (for some field) corresponds to a corresponding, spatially near-uniform step in distance and/or direction. A 1:1 rendering of voltage coordinates as position coordinates, for example, would yield an extremely distorted shape—anisotropically stretched, and/or curved. Moreover, the spatially non-uniform steps in distance and/or direction which exist may be difficult to accurately predict and/or model (e.g., using electromagnetic field modeling), making removing of distortions difficult. For example, some convenient calibration techniques such as correction of errors by use of linear transformations are potentially inapplicable.

Even assuming electromagnetic field non-linearity to be accounted for, any given set of voltage co-ordinates may not uniquely indicate a single position in space, as voltage isopotential surfaces for different electromagnetic fields within a region of interest curved enough to allow (e.g., for some set of three or more electromagnetic fields) a plurality of mutual intersections.

Furthermore, some isopotential surfaces for some pairs of electromagnetic fields may tend to run nearly parallel to one another in at least some locations. Insofar as voltage measurement resolution is limited (e.g., due to safety and/or signal-to-noise considerations), this can lead to uncertainty that undesirably "smears out" spatial position attribution to voltage measurement sets, wherever the two fields are too well aligned for use as sources of independent coordinate information.

Reconstruction Using Combined Multidimensional Scaling and Coherence

Systems and methods of body cavity reconstruction and/or navigation are described in International Patent Application No. PCT IB2018/050192 to the Applicant, filed Jan. 12, 2018; and in International Patent Application No. PCT IB2017/056616 to the Applicant, filed Oct. 25, 2017; the contents of which are incorporated herein by reference in their entirety. Building, for example, on descriptions in those applications, the current inventors have found that the combined use of locally calibrating spatial constraints and/or coherence constraints can be used in some embodiments of the present invention. Locally calibrating spatial constraints, in some embodiments, are provided by any parameters which constrain how different positions from which voltage measurements are obtained relate to one another. Coherence constraints, in some embodiments, constrain the spatial frequency of the main components of a transformation transforming measured values to position estimates. For example, the combined use of locally calibrating spatial constraints and coherence constraints may be used to overcome some of the above-described potential drawbacks of non-linear electromagnetic fields for use in body cavity navigation and/or reconstruction. Herein, the terms "constraint", "constrain", and "constraining" are used to refer to indications providing position-related information, and/or to the use of such indications by a computer-implemented algorithm, e.g., to create a reconstruction and/or locate a position within a reconstruction. In some embodiments, constraints are used in the particular context of an algorithmically derived transformation from a set of measurements taken in some physical space, to a set of positions (in that physical space) that the measurements are determined to correspond to—without relying on knowing the correct set of positions in advance. The constraints constrain how the measured properties are transformed to positions in physical space. The algorithmic derivation of the transformation, in some embodiments, expresses the constraints as cost functions (also referred to herein as error functions or penalty functions, with "more error" "more cost" or "more penalty" being understood as describing the relative value assigned to the cost functions of transformations which are relatively less satisfactory). The more the constraint is violated, the greater the cost (error, or penalty). The algorithmic derivation of the transformation, in some embodiments, seeks a transformation that minimizes (relative to other candidate transformations) the cost function. It is to be understood that constraints and constraining are not necessarily absolute. For example, constraints may be partially satisfied, optionally as measured by an appropriate weighting function (which may adjust the relative importance of different cost functions); and/or constraining may comprise reducing differences in a result relative to a constraint, e.g., by reducing the output of a cost function.

Use of locally calibrating spatial constraints, in some embodiments, optionally comprises the use of multi-dimensional scaling methods (MDS), which allow conversion of measurement distances (in whatever suitable metric, e.g. Euclidean distance or geodesic distance) into a mathematical space placing such measurements in a way that preserves those distances. The mathematical space does not necessarily, correspond to a 3-D volume. In some embodiments, additional dimensions such as heartbeat and/or respiratory phase are taken into account, allowing, e.g., construction of a phase/position space to which measurements are localized.

In some embodiments, inter-electrode distances of electrodes mounted on a catheter probe may serve as locally calibrating spatial constraints. For example, in embodiments and/or conditions where the probe adopts a single well-defined shape, all these distances can be treated as constraints on locations associated with any two measurements taken while the probe was in a certain position (e.g., substantially simultaneously). More particularly, the determined distance between locations associated with two electrodes is constrained to resemble the distance known to exist between the electrodes on the probe. For example, the problem of reconstruction is solved by finding a transform T such that $|T(X_i)-T(X_j)| \approx d_{ij}$, (that is, the two sides of the expression are approximately equal) wherein $d_{ij}$ is a distance between two electrodes, and $X_i$ $X_j$ are measurements made at the two electrodes while they remain in the same position (e.g., simultaneously).

For simplicity of description, sets of simultaneous measurements from corresponding electrodes of a fixed-shape probe are often used in embodiment examples described herein. However, it should be understood that other configurations of sensors, and/or other methods of constraining spatial relationships between measurements are optionally used in some embodiments of the present invention. For a flexible probe, for example, inter-electrode distances may be treated as flexible in any suitable fashion: for example, by reducing an error cost associated with a reconstructed distance other than a default distance, by modeling changes in inter-electrode distance (e.g., as a function of contact force and/or deployment state), etc. In some embodiments, there may be both rigid and non-rigid portions of a probe, for example, a plurality of rigid parts flexibly interconnected. One example of this is a lasso catheter, which has a distal end that can bend into a loop shape composed of segments. Optionally, distances between each electrode and its neighbor on the rigid part may serve as a constraint, while distances between electrodes on different rigid parts are weighted with less influence, or unused.

In some embodiments, known distances used as constraints during reconstruction include distances between electromagnetic field generating electrodes. These electrodes may also be electrodes positioned along a catheter with known spacing between them. These known distances are also referred to herein as "local calibration information": e.g., when each of a pair of electrodes, fixed at a known distance from each other, makes a measurement of an electromagnetic field at about the same time, the known distance between them optionally calibrates the electrical field gradient between their particular measuring positions.

Used alone, local calibration information may preserve local distances well, including calibrating for gradient non-linearities in regions where the size of the gradient is steeply varying as a function of position. However, local calibration alone may allow "wandering" of reconstructed features further apart from each other (e.g., due to cumulative effects of measurement noise), possibly resulting in highly distorted final reconstruction shapes. Optionally, one or more additional techniques is used to reduce such distortions.

In some embodiments, use of constraints on relative positions of sensors (e.g., electrode distances) is supplemented with use of constraints on the spatial coherence that the measurements are expected to have. That is: two measurements made at nearby regions in space are assumed to also produce measurement values which are also "nearby" under some metric (and/or vice versa). This can be expressed as $\Delta X_{ij} \propto \Delta Y_{ij}$, where $\Delta X_{ij}$ is a distance in measurement space between two values i, j of measurements (optionally, each value is a vector comprising a plurality of measurements) made at two electrodes while they remained in the same position (e.g., simultaneously); and $\Delta Y_{ij}$ is a distance (in physical space) between the two locations i, j of the two electrodes, within the body cavity to be reconstructed Y. Optionally, temporal coherence is also assumed. For example, even if there are two roughly equivalent position fits to a measurement considered independently, one may be more reasonable than another based on measurements taken before and afterward, which can be assumed to have been taken "nearby".

The problem of estimating a catheter position based on electromagnetic field measurements may be understood as the problem of finding a suitable transform to convert electromagnetic field measurements into positions (also referred to herein as measurement-to-location transform). Considering either local calibration alone or coherence alone, there may be a plurality of transforms T that transform electrical readings to locations (i.e., transforms T(X) producing estimated positions Y'). However, some of these may fail to sufficiently satisfy Y'≈Y (that is, many possible reconstructions Y' wouldn't look much like the reality Y). Coherence doesn't necessarily provide scale, for example, while distance constraints alone are vulnerable to cumulative distortions from measurement noise. In some embodiments, local calibration (e.g., MDS results) and coherence are combined to find a transform T based on minimization of suitably weighted joint error (or cost) in satisfying both the coherence condition and local spatial constraints. The less a condition is satisfied by some transform, the more error (cost) that condition is said to generate.

For example, error (also referred to herein as cost) with respect to local spatial constraints is optionally found from $|T(x_i)-T(x_j)|=\Delta Y'_{ij} \approx \Delta Y_{ij}$, where the error is in the deviation of distances in Y' from known real-world distances in Y (e.g., error is |Y'−Y|, or another suitable error metric). Only some of the distances in Y are actually known however; e.g., those between electrodes on the same probe making measurements from the same position. Accordingly, the transform T, in some embodiments, is selected to reduce some cost function that increases according to an increasing difference between $|T(X_i)-T(X_j)|0$ and $d_{ij}$ (over the set of available measurement pairs where the distance $d_{ij}$ between two sensors is known). In embodiments where phasic temporal information is also reconstructed, there can be added conditions, such as assuming that a probe in contact with tissue is essentially fixed in spatial position as it "moves" (in time) through different phases of heartbeat and/or respiration.

Similarly, error with respect to coherence is optionally found from $\Delta X \propto \Delta Y'' \approx \Delta Y'$, where the error is in the differences in Y' from the nearest available coherence-modeled output Y" (e.g., error is |Y'−Y"|, or another suitable error metric). Minimization of error (cost) is by any suitable technique, for example, statistical analysis and/or gradient descent. A coherence cost function, in some embodiments, applies a greater cost to sudden (as a function of position in space) changes in a measurement-to-position transform than to gradual changes in the same transform. For example, the transform may be decomposable to low spatial frequencies (corresponding to gradual changes) and high spatial frequencies (corresponding to sudden changes). High frequencies are optionally given a greater cost than low frequencies. As a result transforms that are "smoother" may be preferred. In some embodiments, both a spatial frequency-based cost function and a distance-based cost function are used jointly. Due to interactions among the cost functions, a transform that changes more suddenly may be preferred to avoid "paying the cost" associated with violating the known-distance constraint—and/or vice-versa.

In addition to describing methods using combined local calibration and coherence, International Patent Application No. PCT IB2018/050192 describes optional use of numerous sources of additional information useful to guide reconstruction and/or navigation. Any of these sources is optionally used in some embodiments of the present invention. For example, in some embodiments, the additional information comprises known anatomical data. Optionally, the anatomical data is complete and fairly detailed, such as from segmentations of MRI or CT data (of the patient and/or of atlas information, optionally atlas information matched to patient characteristics such as age, weight, sex, etc.). Optionally, the anatomical data is partial; for example, comprising specifications of relative distances between anatomical landmarks. In some embodiments, a transform may be constrained to transfer measurements taken at the anatomical landmarks to positions distanced from each other by a distance known (from the anatomical data) to exist between the landmarks.

In some embodiments, landmarks are identified by their effect on movement of the probe itself (e.g., the probe's movement while partially inserted to a pulmonary vein root is limited by the circumference of the vein). Optionally, another method of identifying a landmark is used, for example, based on characteristic dielectric and/or electrical conduction properties in the vicinity of the landmark.

In some embodiments, maps of how the measurement values are expected to distribute in space (at least approximately) are used as constraints. For the case of voltage-guided navigation techniques, this can be based, for example, on simulations of electrical field voltages in space, wherein the simulations may incorporate descriptions of electrode configurations and/or body tissue dielectric properties.

It is noted that electrical fields may vary as a result of phasic motions such as heartbeat and/or respiration. International Patent Application No. PCT IB2018/050192 describes optional methods of introducing corrections for such phasic motions which are optionally used in conjunction with some embodiments of the present invention.

Use of High Multiplicities of Electrical Fields

Apart from the use, in some embodiments, of reconstruction techniques suitable for use with non-linear electrical fields, some embodiments of the present invention make use of a relatively large multiplicity of electrical fields, compared with a more traditional reconstruction/navigation scenario mapping three crossing electrical fields to three corresponding spatial axes. For example, in some embodiments, at least 4, 6, 8, 10 or another larger or intermediate number of intrabody electrodes are used to generate at least 4, 10, 15, 20, 25, 30, or another larger or intermediate number of distinguishable electrical fields. Herein, electromagnetic fields which are "crossing" extend through a same region of space. The term "crossing" does not restrict to any particular angle of intersection, or range of angles. Crossing fields may be substantially aligned in some regions. Optionally, electrical fields are distinguished from one another by generation at different frequencies, and/or using another suitable method of channel definition such as time-switched multiplexing. Generally, there is expected to be sufficient bandwidth between about 10 kHz and about 1 MHz that simultaneous use of multiple frequencies is enabled for 30 or more different electrical fields. With use of more electrical fields, the instances and/or severity (e.g., degree of ambiguity) of "degenerate" cases where the same set of voltage measurements point could be mapped to a plurality of spatial positions potentially decreases. The different measurements potentially also serve to better average out sampling error: for example, effects of random noise in measurements may be reduced as more electrodes are combined to determine a position.

Features of Near-Target Sites of Electrical Field Generation

Herein, positioning of intrabody electrodes in the CS for generation of electrical fields used to reconstruct and/or navigate in the LA is used as an example. It should be understood that in some embodiments, other target lumens are navigated using electrical fields generated from other intrabody electrode positions. In selecting positions for electrical field generating, intrabody electrodes in other applications, the criteria of (1) electrical stability, (2) extent allowing generation of spatially distinct fields, and/or (3) proximity to the region targeted for reconstruction/navigation are optionally applied, for example in view of principles now described specifically with respect to the CS and LA.

Electrical stability: the relative position stability of the CS is mentioned above. The atrioventricular groove, in which the CS lies, is relatively stable in part because it surrounds the relatively fixed structures of the mitral valve (although the mitral annulus itself undergoes some changes in geometry within and/or between beats). Accordingly, an electrode located fixedly in the lumen of the left atrium (that is, in a position not influenced by cardiac tissue contractions) should experience relatively stable electrical fields generated by electrodes in the CS.

Moreover, electrically, intrabody electrodes typically provide the potential advantage of stable electrical contact with their surroundings. This contrasts with body surface electrodes, which can be subject to electrical contact changes from causes such as: peeling and/or pressure applied during a procedure, drying out, perspiration, and/or changes in patient posture during the procedure.

Overall extent of electrical field generation: Another feature of the CS which makes it particularly suitable for use with LA applications, in some embodiments, is its considerable angular extent relative to the LA interior. For example, electrical field-generating pairs (or other sets) of electrodes are optionally defined which can generate electrical fields oriented significantly more than about 45° (for example, about 90°) apart from one another. This helps ensure that iso-voltage surfaces from at least some electrical fields will intersect at angles sufficiently far from parallel that information clearly distinguishing at least two of the three spatial axes can be extracted.

Proximity: electrical fields generated from body surface electrodes have a potential disadvantage for stability in a target region compared to fields generated from the CS, because they are influenced by a much greater thickness of non-relevant tissues. Patient differences in anatomy (weight, sex, size, etc.) can thus have a large effect on results. By using fields generated in the CS, and almost immediately adjacent to the LA, many of these differences become much less important, even negligible.

Also reduced, in some embodiments, are changes occurring during the procedure; for example, due to changes in hydration state, and/or phasic changes due to breathing. Global heart movement during breathing is followed by the CS, so electrical fields established from the CS within the LA are relatively unaffected by the breathing. Body surface electrodes, on the other hand, are typically moved relative to the heart by breathing movements. Changes in patient posture can also have effects on the shape of electrical fields generated by body surface electrodes, e.g., due to redistribution of body mass and/or skin surface as posture changes.

In some embodiments, proximity increases field strength, which is a potential benefit for resolving measurement changes associated with small electrode movements. In the case of the CS and LA, the inventors have found that measurement noise encountered with body surface electrodes that restricts positioning resolution to about 1 mm is potentially reduced with CS electrodes, to a little as between 0.01 mm and 0.1 mm. Herein, positioning resolution refers particularly to the distinguishability of adjacent positions (ignoring, for example, potential distortions in reconstructed shape compared to actual shape). In some embodiments, positioning precision (e.g., reproducibility of positioning) actually achieved is restricted by other considerations, for example, tissue movements. Positioning precision, in some embodiments, is within about 15 mm, 10 mm, 5 mm, 3 mm, 2 mm, 1 mm, 0.5 mm, or another intermediate or smaller amount.

An aspect of some embodiments of the present disclosure relates to use of a first intrabody electrode probe to measure voltages of electrical fields produced by electrodes of a second intrabody electrode probe, for use in body cavity reconstruction and/or navigation by movements of the second intrabody probe.

In some embodiments, electrodes of a probe moving around in a body cavity are used to generate a plurality of electrical fields at different frequencies. Voltages from these fields measured from electrodes of a catheter positioned in the CS are used as indications of the positions of the electrodes that generated the fields.

Before explaining at least one embodiment of the invention in detail, it is to be understood that the invention is not necessarily limited in its application to the details of construction and/or the arrangement of the components and/or methods set forth in the following description and/or illustrated in the drawings. The invention is capable of other embodiments or of being practiced or carried out in various ways.

Figure 6:
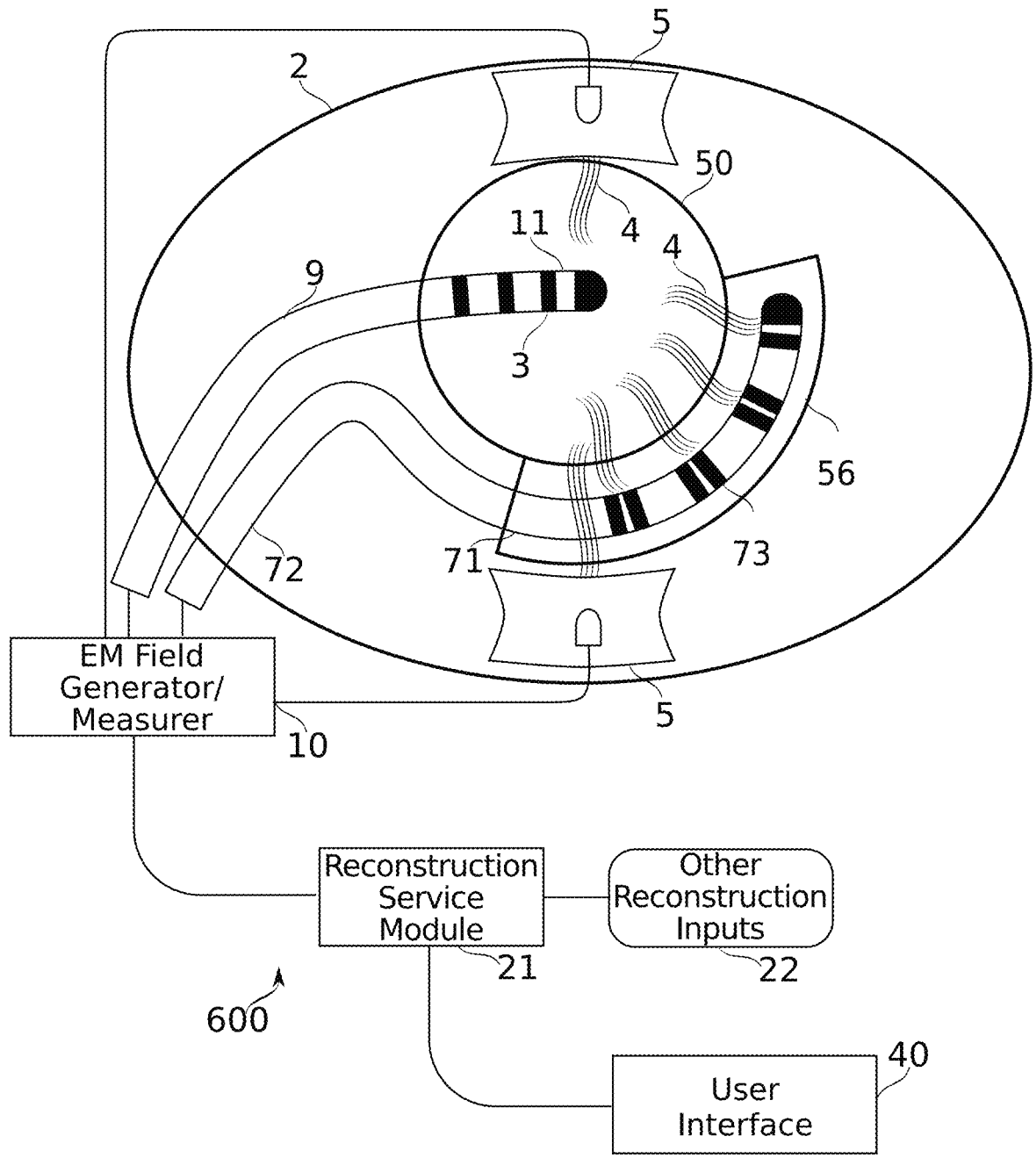
FIG. 6 is a schematic diagram of a system configured for carrying out the method of FIG. 1, according to some embodiments of the present disclosure.

Reference is now made to FIG. 1, which is a schematic flowchart of a method for reconstruction of and/or navigation within a target body cavity (e.g., cavity 50 of FIG. 6), according to some embodiments of the present disclosure. Reference is also made to FIG. 6, which is a schematic diagram of a system 600 configured for carrying out the method of FIG. 1, according to some embodiments of the present disclosure. According to some embodiments, navigation may include or may refer to estimating a position of a probe within a target body cavity.

At block 110, in some embodiments, a plurality of electrical fields 4 (e.g., crossing electrical fields) are generated at least partially using electrical field generating intrabody electrodes 73 (which together comprise an electrode array). Intrabody electrodes 73 may be positioned at stable intrabody positions within body 2, and in proximity to the target body cavity 50. In FIG. 6, electrical fields 4 are drawn arbitrarily to indicate that they reach into target body cavity 50; more detailed discussion of electrical field shape is found, for example, in relation to FIGS. 3A-3B and 4.

In some embodiments, the electrical fields 4 are time varying electrical fields generated at distinct frequencies (e.g., within the range of about 10 KHz to about 1 MHz). Electrical fields 4 are optionally generated across a total potential difference of about 1 V or less, consistent with restriction of electrical current to levels that ensure patient safety. In some embodiments, at least 6, 8, 10 or another larger or intermediate number of electrical field generating intrabody electrodes are used in generating at least 3, 4, 10, 15, 20, 25, 30, or another larger or intermediate number of distinguished (e.g., frequency-distinguished) electrical fields 4. Electrical fields 4 may include two or more fields having a common frequency (for example, they could be distinguished by operating at different, e.g., interleaved, times). Electrical fields 4 of each given frequency are optionally generated from any suitable number of electrical field generating intrabody electrodes 73 in any suitable configuration. For example, there may be a first group of electrodes, comprising one, two, three or more electrodes participating in generating the electrical field in phase with one another; and a second group of electrodes, comprising one, two, three or more generating the electrical field in phase with one another, but in a phase opposing (or otherwise shifted from) the phase of the first group. Optionally, one or more body surface electrodes 5 (i.e., electrodes applied to the surface of body 2) is coupled together with at least one electrical field generating intrabody electrode 73 to generate at least one of the electrical fields 4; e.g., with the body surface electrode 5 acting as a ground electrode. Optionally, at least one electrical field 4 is generated from two sets of differently-phased (e.g., oppositely-phased) electrical field generating intrabody electrodes (at least one electrode per set), and at least one body surface electrode 5 which is optionally configured to act as a ground electrode for all the sets. Optionally, moreover, individual electrical field generating intrabody electrodes may be used in the generation of electrical fields of mutually different frequencies. In some embodiments, electrical fields 4 are controlled and/or powered from electrical field generator/measurer 10. It should be noted that electrical fields 4 which are generated by electrical field generating intrabody electrodes 73 are preferably generated using parameters of electrical configuration and/or safety than electrical fields generated using just body surface electrode 5; e.g., lower voltages, lower current, and/or greater electrical isolation. For simplicity, electrical field generator/measurer 10 is drawn in FIG. 6 as comprising the interface to all electrical elements applied to and/or inserted within the body 2. However, it should be understood that functions of electrical field generator/measurer 10 are optionally divided among any suitable number and arrangement of measurement circuits, controllers, power supplies, etc. Moreover, there are optionally other catheter-related functions such as ablation, force sensing, etc. which are handled by additional modules of system 600, not shown.

In some embodiments, "proximity" between electrical field generating intrabody electrodes 73 and the target body cavity 50 indicates a minimum distance between one or more electrodes in target body cavity 50 and at least one electrical field generating intrabody electrode 73. This minimum distance may be, for example less than about 5 cm, 3 cm, 2 cm, 1 cm, or less than another distance. In some embodiments, "proximity" indicates that the electrical field generating intrabody electrodes 73 are positioned along an extent of an outer wall of the target body cavity 50 (these clarifying specifications may be applied to the word "adjacent" as the word is used herein).

In some embodiments, the intrabody positions of intrabody electrodes 73 comprise positions within the CS 56 (e.g., for embodiments where the target body cavity 50 comprises an interior of a left atrium and/or left ventricle). Optionally, reaching the intrabody positions comprises inserting a portion 71 of a catheter 72 comprising the electrical field generating intrabody electrodes 73 into the CS 56. In some embodiments, an electrode array including electrodes of portion 71 extends further along catheter 72 to a larger extent of the CS than shown. Optionally, the electrode array includes electrodes which are positioned in the right atrium and/or vena cava when some of its electrodes are placed in the CS. In some embodiments, another anatomical structure is used to help define the intrabody positions, e.g., the esophagus and/or the septal wall. A potential advantage of using more electrical field generating intrabody electrode sites is to increase the distribution range of the electrodes in one or more dimensions. The increased distribution range potentially contributes to improve resolution and/or accuracy of the navigation and/or reconstruction. It should be noted that the portion of the CS in which electrodes are positioned does not necessarily extend just in a single plane (i.e., as a part of a flat ring would extend); there is potentially also distribution of electrodes along an axial extent (i.e., axial extent like that of a segment of a helix).

At block 112, in some embodiments, electrical fields 4 induced from the electrical field generating intrabody electrodes are sensed (or otherwise measured) inside target body cavity 50. In some embodiments, sensing electrical fields may include measuring voltages (or another electrical characteristics) using the electrodes of probe 11. In some embodiments, sensing electrical fields may include measuring at least one property of the electrical field, e.g., of each of a plurality of electrical fields, for example: of voltages and/or impedances of the a plurality of electrical fields.

The electrical fields may be sensed by electrodes (as an example of sensors more generally) positioned within the target body cavity, for example, electrodes 3 in the probe section 11 of a catheter 9 (herein, catheter 9 is also referred to as the mapping catheter 9; that is, the catheter which makes position measurements used in determining a reconstruction). The electrodes 3 of probe 11 form together an electrode array. The electrodes of probe 11 may be referred to as "sensors", in reference to their use, in some embodiments, for sensing properties of electrical fields. Optionally catheter 9, in addition to its use as a mapping catheter, comprises an ablation probe, or another probe for which electrically-guided navigation within the target body cavity is to be carried out. In some embodiments, electrodes 3 comprise one or more ablation electrodes, e.g., an electrode configured for use in RF ablation.

In some embodiments, sensing or measuring is from a plurality of electrodes 3. Optionally, voltages associated with each electrical field frequency are dissociated from one another by suitable electrical and/or digital filtering and/or analysis methods. Each electrode 3 thereby is associated with a plurality of sensed values of parameters characteristic of the electrical field (e.g., voltages and/or impedances) which vary over time, and, more particularly, vary over time as probe 11 is moved within target body cavity 50.

In some embodiments, at least two of electrodes 3 are in known spatial relationships with one another, for example, at known (optionally fixed) distances from each other. Herein, electrodes at known fixed distances from one another are used as a simple example of known spatial relationships. International Patent Application No. PCT IB2018/050192 describes other types of known spatial relationships which are optionally used in some embodiments of the present invention.

At block 114, in some embodiments, the target body cavity 50 is reconstructed from the sensed data, e.g., by reconstruction service module 21. Sensed data may include any data sensed or measured as described above. In some embodiments, block 114 may include estimating the position of probe 11 within a target body cavity 50, e.g., based on sensed data. Sensed data may include sensed electrical fields, voltages and/or another electrical characteristic.

In some embodiments, the reconstructed body shape and/or the position of the probe is displayed to a user (e.g., physician), e.g., using user interface 40.

Reconstruction service module 21 may refer to any module configured to reconstruct a body cavity, for example using one or more reconstruction methods as described herein or as described in International Patent Application No. PCT IB2018/050192; for example, a method making combined use of multidimensional scaling and coherence modeling such as is described in the section entitled Reconstruction using Combined Multidimensional Scaling and Coherence herein. For example as there described, combined use of multidimensional scaling and coherence modeling potentially enables reconstruction of a body cavity shape even from highly non-linear electrical fields, such as may be generated by electrodes located adjacent to the body cavity itself. Known inter-electrode distances of electrodes on probe 11 may provide local calibration information, for example, while a coherence model provides additional constraints that help knit together the reconstruction's overall shape. Reconstruction service module 21 optionally includes computer circuitry configured to perform such methods. Optionally, any suitable additional reconstruction input 22 is provided, for example, a target body cavity model (a 3-D model) created based on CT and/or MRI data from a patient, and/or matched to a patient from atlas information, e.g., based on parameters such as age, size, weight, and/or sex. Optionally, a 3-D model of the target body cavity obtained from previous intrabody probe-position mapping (that is navigation and/or reconstruction, for example as described herein) is used. Other types of additional reconstruction inputs 22 used in some embodiments of the current invention are described in International Patent Application No. PCT IB2018/050192, for example, in the section entitled Inputs and Functions of a Reconstruction Service Module. Additional reconstruction input 22 is optionally used, in some embodiments, to help further constrain how the body cavity is reconstructed. For example, the 3-D model may be used to set a global scaling for the reconstruction, to set relative positions of certain landmarks (e.g., the trans-septal crossing point, pulmonary vein roots, mitral valve, and/or left atrial appendage of a left atrium), or otherwise provide information that helps in the determining of positions from the probe measurements. In some embodiments, the information is applied by a process of registration, e.g., adding scaling (optionally non-isometrically) and/or rotating to a transform between electrical field measurements and their determined positions, so that the determined positions match positions defined by the reconstruction input 22. The scaling and/or rotating may be selected in order to reduce a cost function that penalizes differences in position between the determined positions and a plurality of positions and/or spatial relationships defined by of reconstruction input 22. The positions and/or spatial relationships defined may comprise, for example, surface areas, and/or characteristic distances among landmarks.

Optionally, the reconstruction created in block 114 is used in navigation of probe 11, e.g., by displaying the position of probe 11 with respect to the reconstruction on a display module of user interface 40, and updating the displayed position on successive iterations of the method of FIG. 1. It should be noted that separate characteristics of reproducibility and fidelity may be distinguished for the reconstruction of the target body cavity. For purposes of navigation, and particularly navigation for purposes of delivery of treatment such as ablation treatment, reproducibility is potentially the more important of the two—e.g., ablations to treat atrial fibrillation (AF) are preferably positioned in well-defined relationships to one another, in order to ensure that they create an effective block of impulse transmission between them.

Fidelity, on the other hand, is optionally allowed to be less exact in a reconstruction. For example, the reconstruction of a target body cavity may include distortions of distance and/or angle compared to the actual target body cavity which, so long as they are not overtly distracting to a user, may be considered negligible and/or acceptable. In this regard, it is noted that users accustomed to navigation of a catheter are already familiar with a certain amount of decoupling between command motions and results produced, e.g., as catheters are forced into certain paths by the structures they traverse. Such users may find small extra twists and/or other spatial anisotropies to be relatively easy to adjust to.

At block 116, a determination is made as to whether or not reconstruction and/or navigation should continue. If so, the flowchart returns to block 110. Otherwise the flowchart ends.

Figure 2A:
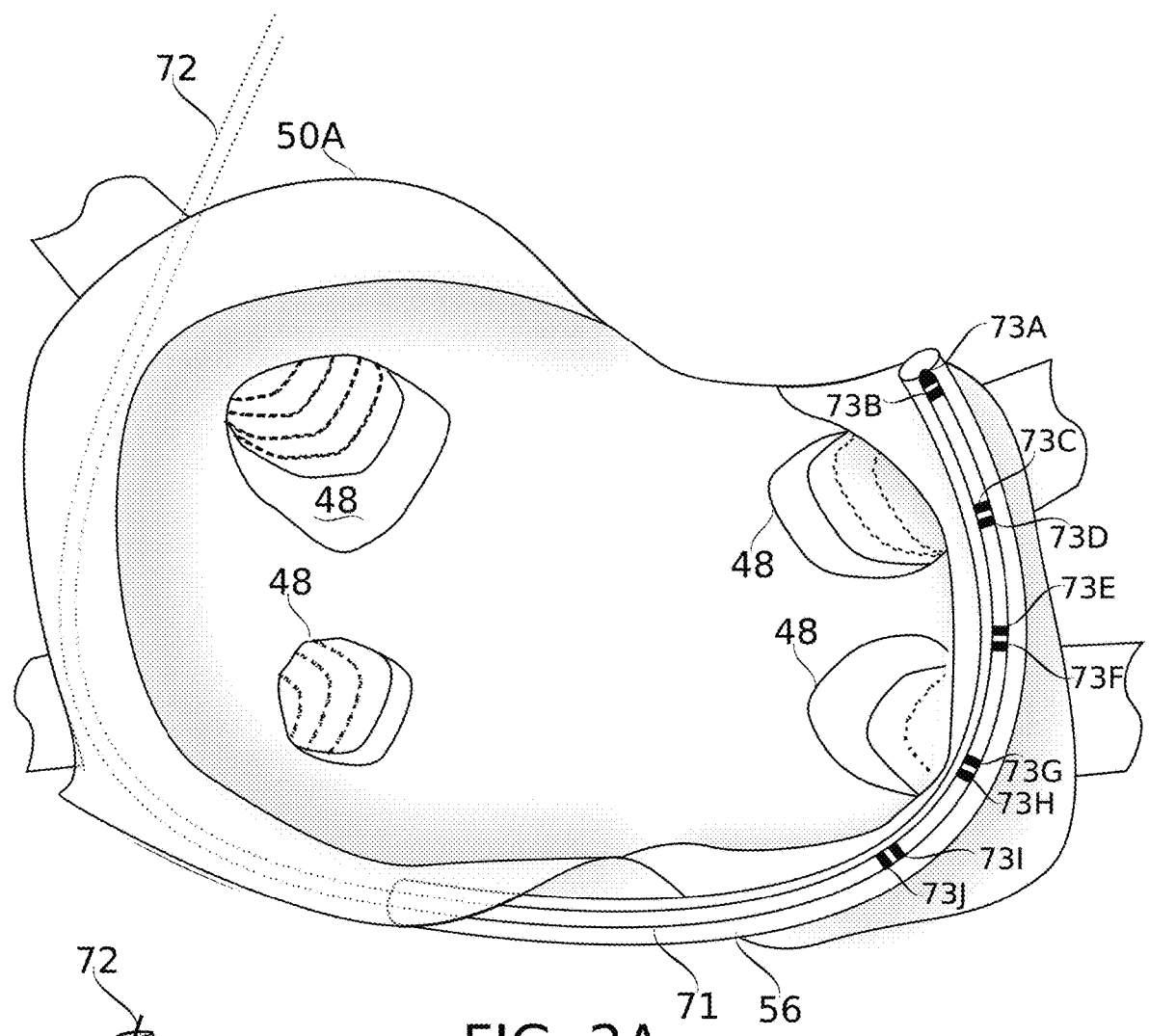
FIG. 2A schematically represents a cutaway view into a left atrium, including an adjacent coronary sinus containing electrodes spaced along a portion of a catheter, according to some embodiments of the present disclosure.
Figure 2B:
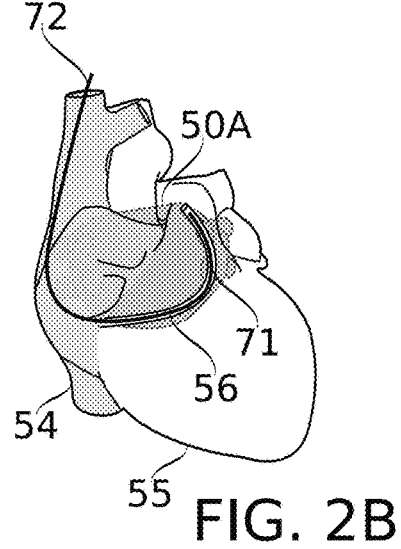
FIG. 2B schematically represents a heart in overview, including features indicated in FIG. 2A, according to some embodiments of the present disclosure.

Reference is now made to FIG. 2A, which schematically represents a cutaway view into a left atrium 50A, including an adjacent coronary sinus 56 containing electrodes 73A-73J spaced along a portion 71 of a catheter 72, according to some embodiments of the present disclosure. Reference is also made to FIG. 2B, which schematically represents a heart 55 in overview, including features indicated in FIG. 2A, according to some embodiments of the present disclosure.

Also indicated in FIG. 2A are roots of the pulmonary veins 48. In FIG. 2B, right atrium 54 is distinguished by its shading. It is noted in particular that coronary sinus 56 extends outside of and along left atrium 50A, near the right hand side of the left atrium in the view shown.

In some embodiments, a catheter 72 is introduced into coronary sinus 56 by insertion from the superior vena cava into the right atrium 54, and from there into the coronary sinus 56 (in FIG. 2A, the view of the right atrium itself is suppressed). Catheter electrodes 73A-73J optionally take up positions similar to those shown, though they optionally extend over a larger or smaller extent of the coronary sinus, according to the design of the electrode catheter 72 (that is, a catheter comprising one or more electrodes configured to generate and/or measure electrical fields and/or electrical field properties) which is selected for use.

Figure 3A:
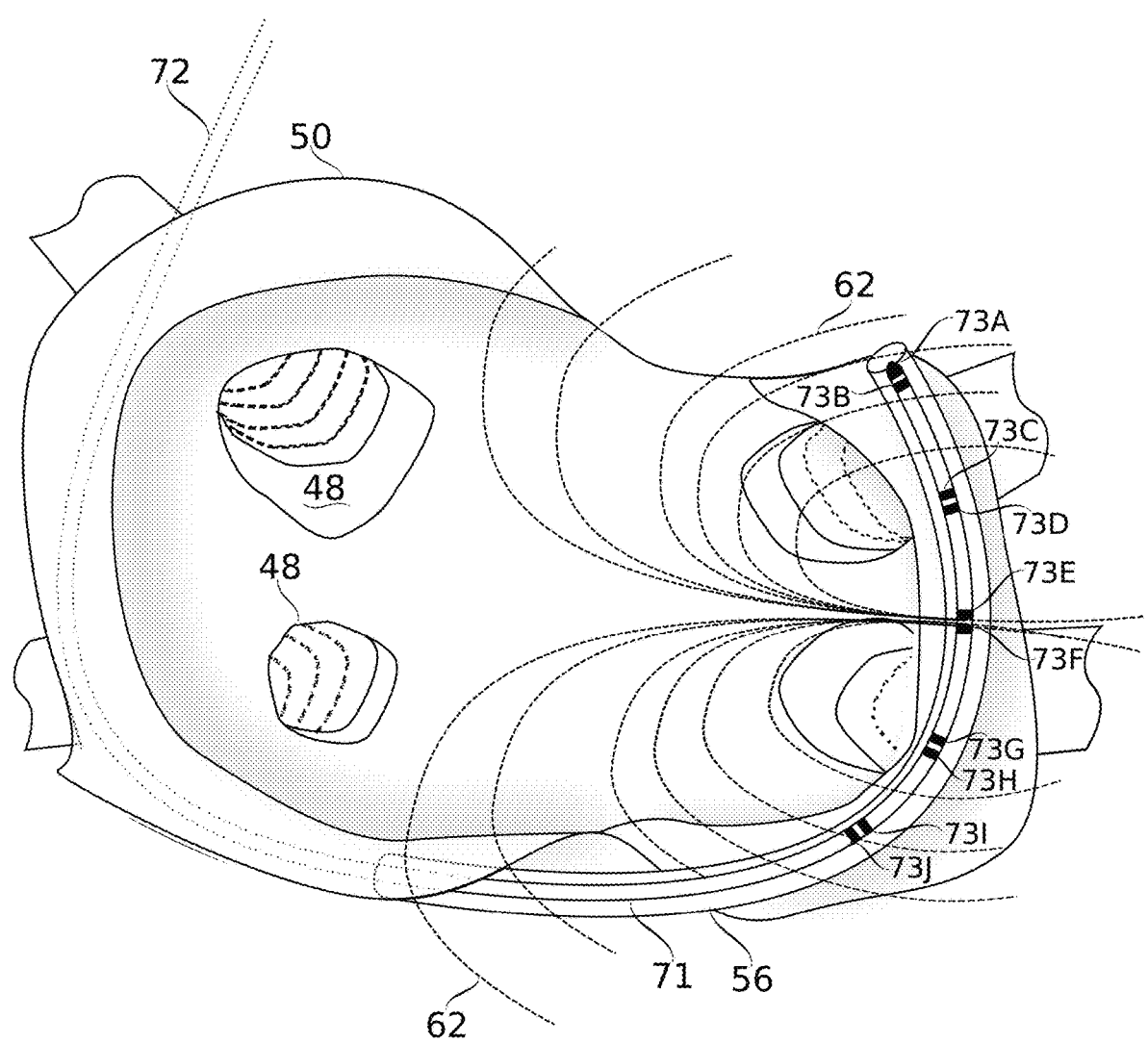
FIGS. 3A-3B and 4 show features of the schematic view of FIG. 2A, with electrical field lines (i.e., voltage isopotential lines) superimposed, according to some embodiments of the present disclosure.
Figure 3B:
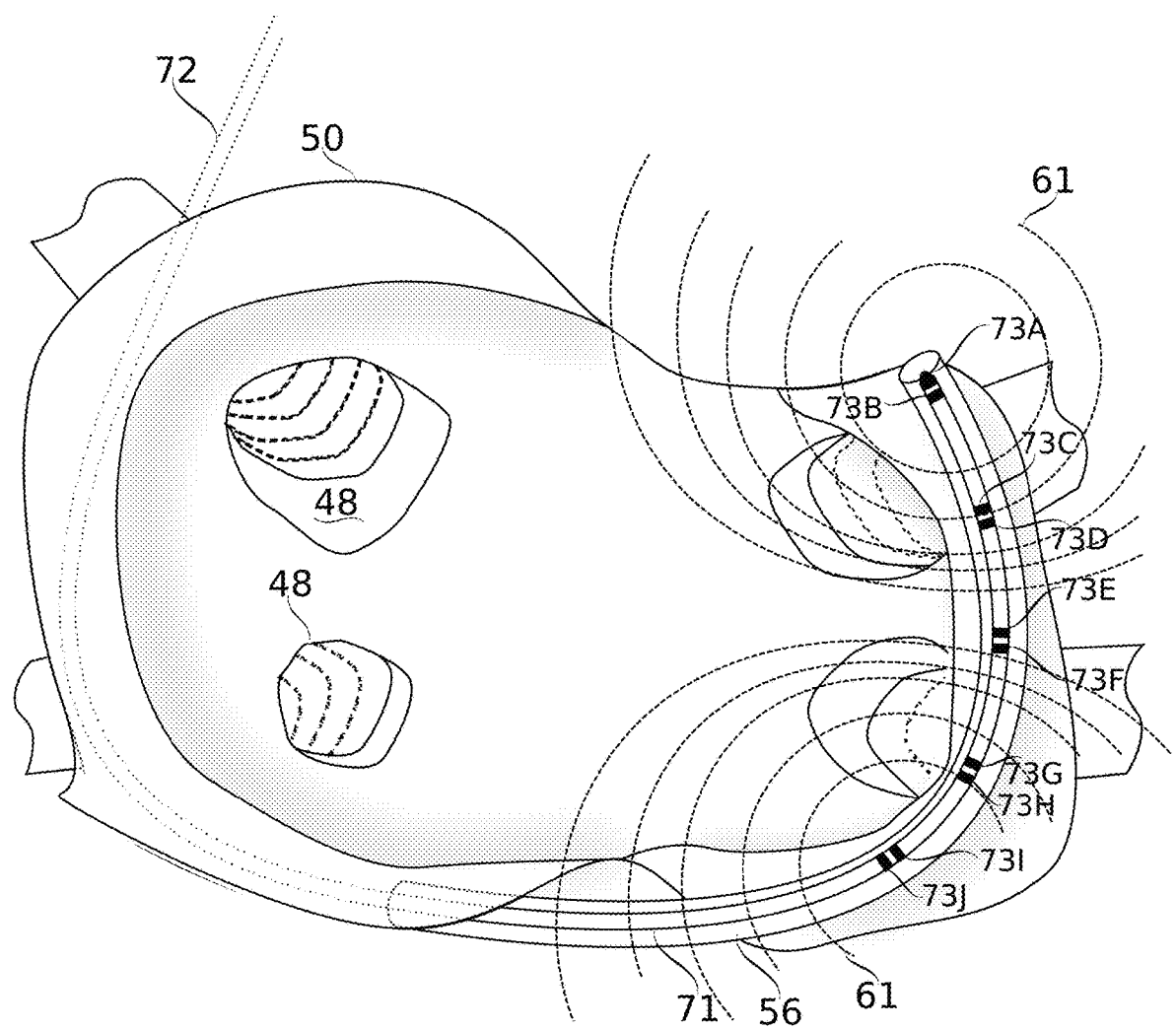
Figure 4:
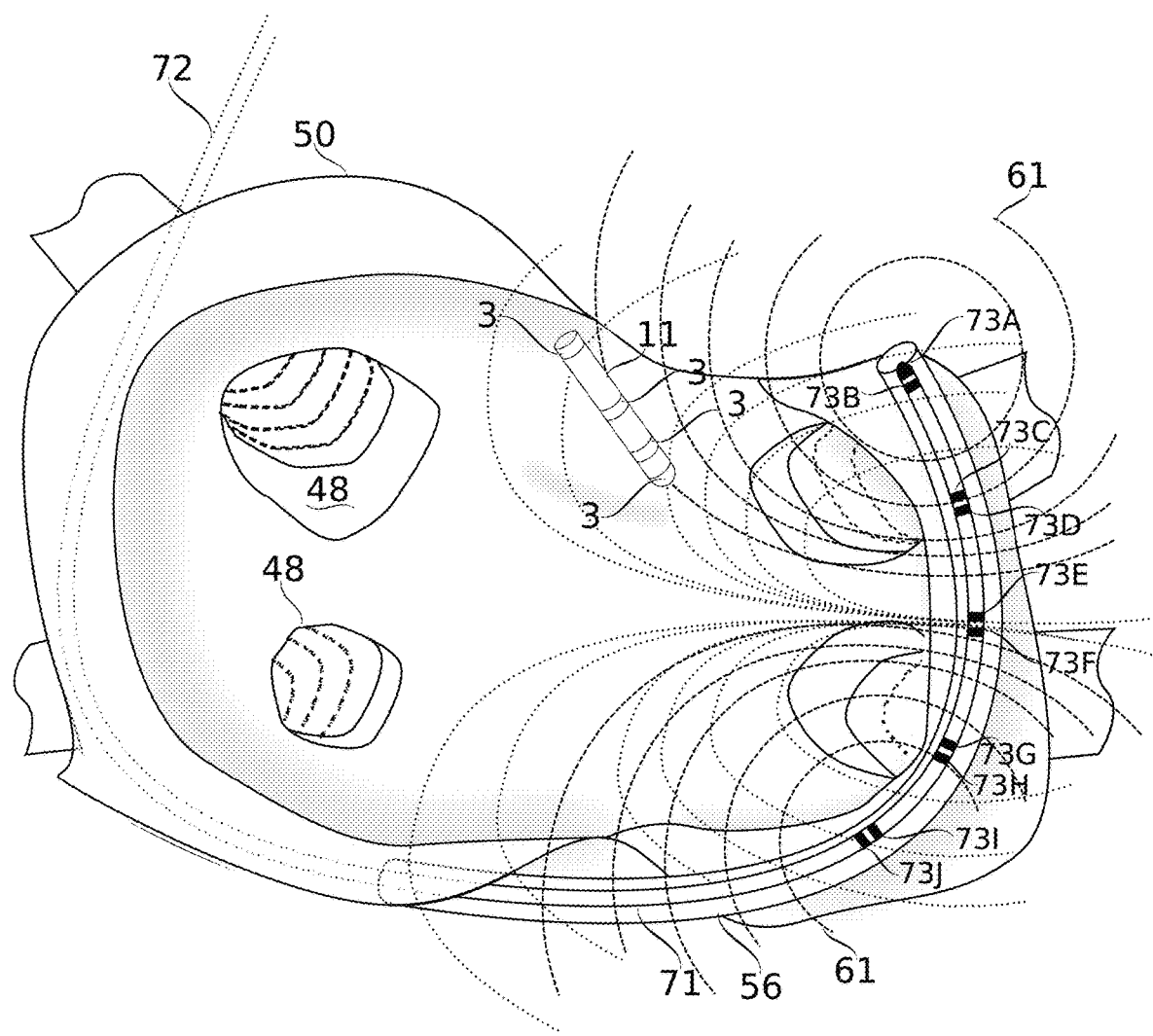

Features of FIG. 2A are shown again in following FIGS. 3A-3B and 4 in relation to examples of electrical field shapes.

Figure 2C:
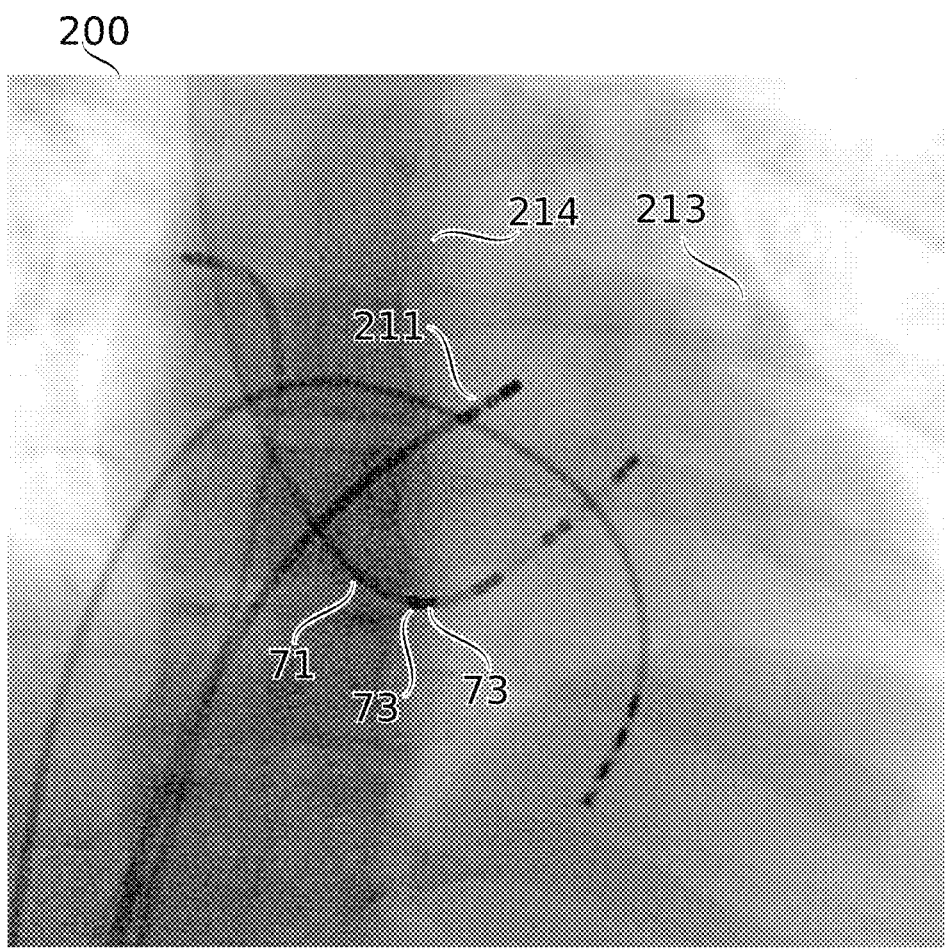
FIG. 2C comprises a radiographic image showing positions of several catheter portions, including catheter portion and its electrodes inserted into a CS of a heart, according to some embodiments of the present disclosure.

Reference is now made to FIG. 2C, which comprises a radiographic image 200 showing positions of several catheter portions, including catheter portion 71 and its electrodes 73 inserted into a CS of a heart, according to some embodiments of the present disclosure. The heart tissue itself is invisible in this image. The position and view of catheter portion 71 are roughly similar to the position and view shown in FIG. 2A. The end of another of the catheters shown (catheter distal portion 211) is positioned within the left atrium. Also indicated for reference and scale are ribs 213, and vertebral column 214.

Reference is now made to FIGS. 3A-3B and FIG. 4, which show features of the schematic view of FIG. 2A, with electrical field lines 62, 61 (i.e., voltage isopotential lines) superimposed, according to some embodiments of the present disclosure.

In FIG. 3A, electrical field lines 62 represent field lines created from two closely spaced electrodes 73E, 73F, being driven at the same frequency with opposite phases. Shown is a "snapshot" of isopotential lines, e.g., as each electrode reaches its respective minimum/maximum voltage. Roughly along a plane perpendicular to a segment directly connecting electrodes 73E, 73F, the two electrodes cancel each other out. Radiating from either side are isopotential contours representing progressively weaker voltages. 2-D contours are shown; in three dimensions, the isopotential contours extend into and out of the page as well (i.e., the contours shown represent partial cross-sections of roughly ovoid isopotential surfaces). It is noted that a single electrode sensing voltages from just this electrical field would report all spatial points on a single isopotential surface as being equivalent. It can also be seen that the isopotential surfaces are very far from being planar.

The electrical field lines 61 of FIG. 3B are created between more distantly spaced electrodes 73A, 73J, each optionally oscillating in voltage at the same frequency, but opposite phase. In this example, the larger electrode separation allows isopotential surfaces, particularly near the electrodes, to assume more spherical shapes.

The voltage isopotential surfaces illustrated in cross-section in FIGS. 3A-3B are examples for illustration purposes; optionally, other isopotential surface shapes are formed. For example, using a row of multiple electrodes with the same frequency and phase may reshape isopotential surfaces to be more nearly parallel to the front defined by the row of electrodes. Using a body surface electrode can also help shape the electrical field, e.g., to a more dome-like configuration.

In FIG. 4, the electrical fields of FIGS. 3A-3B are shown combined. Now, within the left atrium and within single plane, there is just one position corresponding to most of the voltage pairs that electrodes 3 of probe 11 could sense (the second intersection lies outside the left atrium in most cases). It is noted that the isopotential surface intersections (probe 11 is shown at one of them) do not lie in any particularly regular arrangement. From this arises one of the potential difficulties in reconstructing a shape similar to that of the left atrium from a set of measured voltages: even though sets of voltage coordinates measurements can be assigned a definite order in space, they would define an extremely warped shape if simply converted, e.g., to Cartesian coordinates proportional to voltage. Nevertheless, the isopotential surfaces of the pair of electrical fields illustrated does have a potential advantage in that many of the isopotential surfaces cross at fairly large angles (e.g., angles >30°), at least in the cross-sections shown. This is a potential advantage for reducing spatial degeneracy in voltage-based position estimates, since there is a shorter distance that can be moved along an isopotential surface of one of the electrical fields, before there is a detectable change in the voltage measured from the other electrical field. It should be noted that desirable properties of any given electrical field (or set of fields) may not be found uniformly in all parts of a space to be navigated. Optionally, many more electrical fields are used, so that the total information over all electrical fields uniquely and precisely identifies locations. Optionally, different subsets of electrical fields (and their originating electrodes) are chosen to cover different areas of the target body cavity. These electrical field subsets may be activated all at once (e.g., at different frequencies). Optionally, different electrical field subsets are activated at different times, depending, for example, on the current position of a mapping catheter 9.

Figure 5:
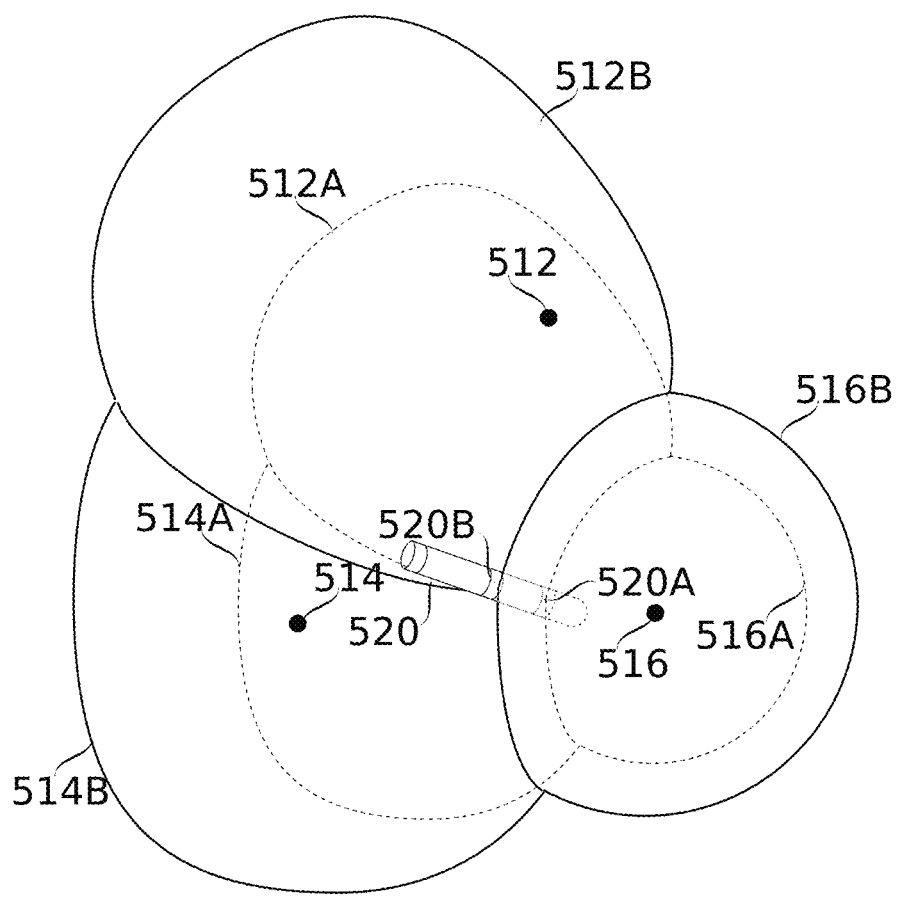
FIG. 5 schematically represents two electrodes of known fixed distance from each other, each making measurements of voltage fields originating (at least in part) from nearby electrode positions, according to some embodiments of the present disclosure.

Reference is now made to FIG. 5, which schematically represents two electrodes 520A, 520B of known fixed distance from each other, each making measurements of voltage fields originating (at least in part) from electrode positions 512, 514, and 516, according to some embodiments of the present disclosure.

Electrode 520A is shown measuring voltages at a particular region which is at an intersection of each of voltage isopotential surfaces 512A, 514A, and 516A. Electrode 520B is shown measuring voltages at a particular region which is at an intersection of each of voltage isopotential surfaces 512B, 514B, and 516B. Both electrodes are at fixed distances because they are carried together on a catheter probe region 520 (assumed to be a straight region, for purposes of description). While only three different fields are shown in FIG. 5, optionally, a larger number of electrical fields may be created, e.g., by ganging different electrode sets together, involving (or not) body surface electrodes, and/or re-using electrodes to generate electrical fields of multiple frequencies, with each frequency involving different sets of electrodes.

Because the distance between electrodes 520A and 520B is known, the simultaneity of the measurements may be viewed as effectively determining a spatial scale for voltages in the region extending between them, e.g., in mV/mm. For one measurement, and one pair of electrodes, this may not be a completely unambiguous determination, since there may be another pair of three-way intersections having the same voltage values. However, as more measurements are made, and/or if more electrodes are used, the ambiguity lessens, so that only one pair of spatial positions, in general, is consistent with the overall pattern.

Another important use for simultaneous measurements from electrodes at known distances is that with enough samples, the spatial scale assignments begin to limit the range of possible reconstructed shapes. Multidimensional scaling algorithms, used in some embodiments, are implemented by a processor device (e.g., a computer) configured to assign spatial positions to samples, using and preserving known distances between sensors (e.g., electrodes). There may nevertheless be noise associated with measurements that introduce distortions, particularly distortions due to cumulative error. In some embodiments, such errors are reduced by adding another criterion to guide the reconstruction, such as a coherence criterion that helps ensure that the reconstruction assigns nearby spatial positions to be associated with similarly "nearby" voltage measurements, for example as described in the section entitled Reconstruction using Combined Multidimensional Scaling and Coherence herein.

Figure 7:
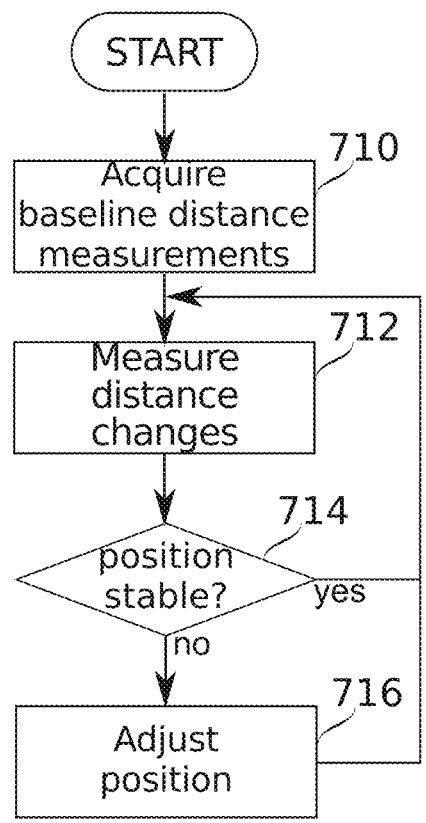
FIG. 7 is a schematic flowchart illustrating a method for monitoring and correction of electromagnetic field generating intrabody electrode placement, according to some embodiments of the present disclosure.

Reference is now made to FIG. 7, which is a schematic flowchart illustrating a method for monitoring and correcting the placement of the electrical field generating intrabody electrodes (e.g., an array of electrodes 73), according to some embodiments of the present disclosure. Herein, electrodes placed in the CS as electrical field generating intrabody electrodes will be described as an example.

The flowchart begins with an intrabody electrode array already positioned in a target position (for example, as a part of a procedure preceding the procedure of FIG. 7). At block 710, in some embodiments, baseline measurements are taken. Baseline measurements are measurements characteristic of distances between electrodes placed to function as electrical field generating intrabody electrodes, and may comprise, for example, voltages. The baseline measurements are optionally of any parameter which is characteristic of a particular inter-electrode distance, and changes when the distance changes. In some embodiments, for example, the baseline measurements are of voltages sensed by a first (e.g., high impedance) electrode, when one or more other electrodes is activated to generate an electrical field (such baseline measurement are also referred to herein as baseline voltages). Additionally or alternatively, currents passing between a plurality of electrodes at generated voltages are used as a baseline measurement. Optionally, actual distances are measured, for example, distances determined from ongoing reconstruction based on voltage measurements. At least one, and optionally all of the electrodes used can be an electrode positioned in the CS. In some embodiments, at least one of the electrodes used in the baseline measurement is positioned at another location. In some embodiments, the other location is also intrabody; for example, one or more points on the septal wall (e.g., at a place where a mapping catheter 9 and/or another catheter used together with it crosses the septal wall).

Optionally, the electrode in the other location is a body surface electrode, for example, a body surface electrode placed on the back (e.g., where it is less affected by movements due to breathing).

A potential advantage of using only intrabody electrodes in baseline (and later) measurements is to avoid the use (and potential disadvantages, at least for certain applications) of body surface electrodes.

At block 712, in some embodiments, the measurement characteristic of distance is repeated (that is, re-measured), and examined for changes from the baseline measurement. In some embodiments, measurement repetition is frequent and automatic from stationary electrodes; for example, every 100 msec, 200 msec, 500 msec, 1 sec, 2 sec, or at another interval. Stationary electrodes may be stationed at the septal wall (for example, on a transseptal sheath), on a body surface, and/or in the CS itself. In some embodiments, measuring is occasional, for example, for running a stability check. In a stability check, an electrode may be repositioned where it was when the baseline measurements were taken. For example, a position near the septal wall can optionally be re-identified by characteristic changes in impedance measured as an electrode crosses the wall, and this identification used as a basis for the stability check. The characteristic impedances (and/or changes therein) optionally are used as a "tag" that identifies where the probe should be in the reconstruction, when that tag is being measured.

Determination of a distance change, in some embodiments, comprises simply noting that a new (e.g., present) measurement is different than the baseline measurement. In some embodiments, the determination of a distance change looks for a sudden step (which potentially indicates a slipping event).

With respect to using CS-to-CS electrode measurements, distance changes, when they occur, may be less pronounced than with respect to other reference electrode positions, since the CS electrodes are optionally all located on the same catheter, and distance changes would be mostly due to changes in the curvature of the catheter as the catheter is (for example) partially pulled from its position in the CS. However, loss of sensitivity due to this potentially decreased signal size is potentially counterbalanced by ordinarily increased stability of CS electrode positions with respect to one another.

In some embodiments, distance changes are measured "virtually". For example, if new results of reconstruction show shifting of the apparent position of theoretically stable positions (e.g., a fossa ovalis on the septal wall or another position that "should be stable"), there may have been a shift in CS electrode position.

At block 714, if the present position of the CS electrodes is stable (that is, has not changed between the measurements made at block 712 and at block 710), the flowchart returns to block 712 for another check. Optionally, the baseline distance measurement itself is occasionally updated at block 710, for example, to correct for slow measurement drift which is not indicative of movement.

Otherwise, at block 716, the position of the CS electrodes is adjusted (that is, the CS electrodes are re-positioned). In some embodiments, adjusting is performed by moving the CS electrode catheter forward and/or backward in place, reducing the difference between the baseline distance measurement and new measurements until a measurement close to the original baseline measurement is restored. Once the distance (and/or distance-characteristic) measurement is restored to baseline, the method loops back again to block 712.

Examples of Use Cases

Use of electrodes on a CS catheter to produce navigation fields has particular potential advantages where the use of body surface electrodes is problematic. Following are a few examples.

Sterile Fields

In some embodiments, use of body surface electrodes is limited because of the need to maintain a sterile field for access into the body. This can arise, for example, with procedures accessing the heart through the chest (e.g., using a subxiphoid approach). One example of this is treatment of ventricular tachycardia, by ablation of the outer membrane of the heart (epicardial ablation). Although the entrance for this procedure is through the chest, there is still a need for mapping and/or navigating in the area of treatment.

Vest Measurements

Technology exists (e.g., as marketed by CardioInsight/Medtronic) for use of a vest comprising electrodes to make electrical measurements allowing localization of "rotors" (re-entrant electrical spiral waves) underlying some cases of atrial fibrillation. In a typical treatment, the vest is used to find the rotor, the area of the rotor is ablated intracardially, and then the process repeats (e.g., 7-8 times) until the rotor is abolished. Use of the vest to locate rotors is incompatible with the use of other body surface electrodes, however. Using electrodes in the CS potentially overcomes this limitation.

Basket Catheters

Another method of rotor location comprises use of an intracardial basket catheter comprising many electrodes (e.g., 64 electrodes). Rotor location by such a method uses position of each electrode as an input. Potentially, accuracy of results is improved by more accurate knowledge of electrode position.

In some embodiments, electrical fields generated from CS-positioned electrodes may allow locating these electrodes, potentially with improved accuracy and/or stability compared to other impedance-based position-finding methods.

Navigation in Regions Near Body Surface Electrodes

Use of the reconstruction method coupling MDS with coherence potentially also assists in other scenarios where an electrode used to generate an electrical field for navigation is positioned close to a navigating region. This can arise, for example in treating the anterior wall of the ventricle, which may be very close to a body surface electrode positioned on the chest. In this location, accuracy of conventional impedance-based navigation relying on linear field configurations is impaired—because the linear approximation becomes very inaccurate. Alternatively, in such a situation, use of the body surface electrode could be dispensed with in favor of using electrical field generating electrodes in the CS.

Replacement for Magnetic Sensing

Magnetic field-based position sensing technologies can be highly accurate, but require specialized catheters (currently, most catheters in the market are devoid of magnetic sensors). The magnetic sensors also tend to be bulkier than electrodes, which may preclude their use in multi-sensor configurations such as 64-sensor basket catheters. Using CS-positioned electrodes to generate electrical fields for impedance sensing potentially provides accuracy competitive with magnetic field position sensing, without the need for unusual catheters and/or bulky sensors.

Nevertheless, in some embodiments of the invention, magnetic field generating elements (e.g., magnetic coils or another magnetic field generating device) may be placed on CS-positioned probes (e.g., replacing electrical field-generating electrodes in any of the embodiments described herein). Magnetic fields generated therefrom may be sensed for determining positions of a second intrabody probe using magnetic field sensors such as coils on the second intrabody probe (e.g., again replacing electric field sensing electrodes in any of the embodiments described herein.

General

It is expected that during the life of a patent maturing from this application many relevant catheter types will be developed; the scope of the term catheter is intended to include all such new technologies a priori.

As used herein with reference to quantity or value, the term "about" means "within ±10% of".

The terms "comprises", "comprising", "includes", "including", "having" and their conjugates mean: "including but not limited to".

The term "consisting of" means: "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The words "example" and "exemplary" are used herein to mean "serving as an example, instance or illustration". Any embodiment described as an "example" or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features except insofar as such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A method of reconstructing a shape of a body cavity by a first probe positioned in the body cavity, the first probe comprising a plurality of sensors, the method comprising:
    measuring electrical characteristics using the sensors of the first probe, when the first probe is at a plurality of locations inside the body cavity, the measuring comprising sensing a plurality of crossing electrical fields generated from electrodes of a second probe positioned inside the body and adjacent to the body cavity; and
    reconstructing the body cavity, based on the measuring, wherein at least two of the plurality of sensors are spaced at a known distance from each other on the first probe, and wherein the reconstruction is carried out using a cost function that assigns costs to distances between reconstructed locations of two sensors, according to a difference between said reconstructed distance and the known distance that separates between the two sensors on the first probe.

2. The method of claim 1, wherein said reconstructing comprises reconstructing an image of said cavity.

3. The method of claim 1, wherein said reconstructing comprises reconstructing a surface geometry of said cavity.

4. The method of claim 1, wherein said measuring is performed at a plurality of locations inside the body cavity, by moving said first probe between locations and sensing said plurality of crossing electrical fields thereat.

5. The method of claim 1, wherein each of the plurality of crossing electrical fields oscillates at a different frequency.

6. The method of claim 1, wherein the electrical characteristics comprise voltages.

7. The method of claim 1, further comprising registering the reconstruction of a shape of the body cavity to a 3-D model of the body cavity.

8. The method of claim 7, wherein the 3-D model of the body cavity is based on imaging data imaging the body cavity.

9. The method of claim 8, wherein the 3-D model of the body cavity is based on atlas information.

10. The method of claim 1, further comprising estimating a position of the first probe relative to the reconstruction, based on the measuring of the electrical characteristics at the location of the first probe when measuring.

11. The method of claim 1, wherein the second probe is positioned in a coronary sinus, and wherein the body cavity comprises a heart chamber adjacent to the coronary sinus.

12. The method of claim 11, wherein the heart chamber comprises a left atrium.

13. The method of claim 11, wherein the heart chamber comprises a left ventricle.

14. The method of claim 1, wherein the plurality of crossing electrical fields comprise at least three crossing electrical fields.

15. The method of claim 1, wherein a body surface electrode acts as a ground electrode relative to at least one of the electrodes of the second probe.

16. The method of claim 1, wherein no body surface electrode are used for said measuring.

17. The method of claim 1, wherein said reconstructing uses also measurement of electric fields generated between body surface electrodes.

18. The method of claim 1, comprising using said sensors of said first probe to navigate in the body to reach said cavity.

19. The method of claim 1, wherein each of said first and second probes include at least three electrodes which generate said fields, measure said fields, or both generate and measure said fields.

20. The method of claim 1, wherein said sensing comprises sensing one of the plurality of crossing electrical fields simultaneously with other ones of the plurality of crossing electrical fields.

21. The method of claim 1, wherein said second probe is curved so that said electrodes thereof do not line in a straight line.

22. The method of claim 21, wherein said electrodes of said second probe extend around at least 25% of a circumference of said cavity.

23. The method of claim 1, wherein said first probe is of a tubular shape.

24. The method of claim 1, further comprising generating said electric fields, and wherein said electric fields are highly curved at said measurement locations with a radius of curvature of isopotential surfaces thereof, of less than 5 cm.

25. The method of claim 24, wherein said electric fields are highly curved with said curvature radius of less than 5 cm in at least 8 cm^3 of said reconstructed cavity.

26. The method of claim 1, wherein said first probe and said second probe are both immersed in a same body fluid.

* * * * *

UNITED STATES PATENT AND TRADEMARK OFFICE
CERTIFICATE OF CORRECTION

| | |
|---|---|
| PATENT NO. | : 11,464,422 B2 |
| APPLICATION NO. | : 16/478486 |
| DATED | : October 11, 2022 |
| INVENTOR(S) | : Yizhaq Shmayahu et al. |

It is certified that error appears in the above-identified patent and that said Letters Patent is hereby corrected as shown below:

On the Title Page

In item (73) Assignee:
"Navix Internatonal Limited"
Should be changed to:
--Navix International Limited--

Signed and Sealed this
Thirty-first Day of January, 2023

Katherine Kelly Vidal
*Director of the United States Patent and Trademark Office*